(12) United States Patent
Lundbäck et al.

(10) Patent No.: US 8,244,510 B2
(45) Date of Patent: Aug. 14, 2012

(54) STATE SPACE MODEL OF A HEART

(75) Inventors: Stig Lundbäck, Vaxholm (SE); Jonas Johnson, Norrtälje (SE)

(73) Assignee: Gripping Heart AB, Stockholm (SE)

( * ) Notice: Subject to any disclaimer, the term of this patent is extended or adjusted under 35 U.S.C. 154(b) by 564 days.

(21) Appl. No.: 12/375,035

(22) PCT Filed: Jul. 6, 2007

(86) PCT No.: PCT/SE2007/050511
§ 371 (c)(1),
(2), (4) Date: Jul. 10, 2009

(87) PCT Pub. No.: WO2008/013497
PCT Pub. Date: Jan. 31, 2008

(65) Prior Publication Data
US 2009/0311656 A1    Dec. 17, 2009

(30) Foreign Application Priority Data
Jul. 25, 2006  (SE) ...................... 0601609

(51) Int. Cl.
*G06G 7/58* (2006.01)
(52) U.S. Cl. .............................. 703/11; 702/19; 703/2
(58) Field of Classification Search .......... None
See application file for complete search history.

(56) References Cited

U.S. PATENT DOCUMENTS

| 6,754,580 B1 | 6/2004 | Ask et al. |
| 7,239,987 B2 | 7/2007 | Lundback et al. |
| 2003/0023319 A1 | 1/2003 | Anderson et al. |
| 2005/0202384 A1 | 9/2005 | DiCuccio et al. |

FOREIGN PATENT DOCUMENTS

| WO | 00/72750 | 12/2000 |
| WO | 01/88642 | 11/2001 |

OTHER PUBLICATIONS

Holden et al. "Reconstructing the Heart", 1995, Chaos, Solitons, & Fractals, vol. 5, Nos. 3/4, pp. 691-704.*
International Search Report dated Dec. 11, 2007, from corresponding PCT application.

* cited by examiner

*Primary Examiner* — Caroly L. Smith
(74) *Attorney, Agent, or Firm* — Young & Thompson

(57) ABSTRACT

A state space model (SSM), being a computer-calculated model, adapted to represent the pumping and controlling functions of a heart that have been determined by a heart cluster state machine simulating the heart, and optionally the circulatory system, of an individual. The state space model includes two groups of separate interacting state machines, the heart muscle cell state machines and the displacement pump state machines.

10 Claims, 10 Drawing Sheets

STATE SPACE MODEL OF A HEART

The present invention relates to a novel State Space Model of the heart to be implemented in investigating methods and databases.

The present application is related to PCT/SE2006/000114 (international filing date Jan. 25, 2006), assigned to the applicant of the present application, that relates to a heart cluster state machine applicable to simulate the pumping and regulating functions of the heart and the circulatory system.

FIELD OF THE INVENTION

The regulating functions of the heart have earlier never been fully understood, nor has the pumping functions of the heart, especially at high heart rates, been able to be explained. The muscular functions are known down to molecular levels as well as the conducting system of the heart and muscle cells. All investigations of the heart and circulatory system are based on observations in relation to other observations with no relations to the mechanics of the heart. This might depend on the belief that the heart is pumping and regulating flow by squeezing functions and thus with more or less no mechanical functions. Because of this all investigating and computer modelling of the heart are focused on the activities of the heart muscles in trying to understand and analyze the functions of the heart. This result in many cases that a lot of investigations with different kinds of observations have to be performed in order to get enough information's to evaluate the function of the heart. These evaluations can still not be used to describe the true pumping and regulating functions of the heart.

The background to the present invention is based upon the insight that the heart appears in its pumping function more like a piston pump or a pressure and suction pump and even more precise as a cluster heart state machine of finite muscle cell state machines and two interacting DeltaV-pump state machines generating a third the DeltaV heart pump with abilities to be controlled by inflow. Further more the construction of the heart has a booster function inherit in the atria and auricular contractions that can result in an increased stroke length of the DeltaV-piston.

BACKGROUND OF THE INVENTION

It is asserted in the theses Lundbäck S., "Cardiac Pumping and Function of the Ventricular Septum", Stockholm, 1986 that the pumping and regulation of the human heart take place in a manner which is at variance with the prevalent view.

According to the cited publication, the healthy heart performs its pumping action without substantially changing its outer contours and volumes.

As a result of the theory presented in the above-mentioned publication regarding the heart's pumping and regulating function a new class of pumps has emerged, a so called dynamic displacement pump or delta ($\Delta$) volume pump (abbreviated as $\Delta$V-pump).

The principles of a $\Delta$V-pump will now be described with references to FIGS. 1a and 1b. The pump comprises an upper cylinder 2 with diameter d1 and a lower cylinder 4 with diameter d2, where d2>d1. These two cylinders are connected to each other via a third cylinder 6 that is freely movably arranged between the upper and lower cylinders. The movable cylinder 6 is provided with a valve 8 at its lowest part that corresponds e.g. to the Mitral valve in the heart. The volume above this valve is defined as the atrial volume (Va) and the volume below the valve is defined as the ventricular volume (Vv). The lower cylinder is provided with an outflow valve 10 at its lowest part that corresponds e.g. to the aortic valve in the heart. As can be seen from FIG. 1b is a ring-shaped cylindrical volume gradually obtained between the movable cylinder and the inner wall of the lower cylinder when the movable cylinder is moved down, $\Delta$V in the figure. This results in that the volume Va+Vv decreases with the volume $\Delta$V when the movable cylinder moves between its upper position and its lower position.

A source of energy (not shown in the figures) is adapted to move the movable cylinder from its upper position to its lower position, which defines the length L of a stroke for the pump. When the movable cylinder moves down to its lowest position the outflow valve is forced to open and a part of volume Vv is expelled. The movable cylinder is then released from the source of energy and can return to its upper position by hydraulic forces created by pressure gradients if there is an inflow to the pump. This is referred to the DeltaV-function ($\Delta$V-function). If Av and Aa designates the cross-sectional areas of the upper and lower cylinder, respectively, $\Delta$V equals L(Av-Aa).

WO-01/88642 relates to a computer based system adapted to create a representation of the pumping action of a heart by using a mathematical model of the functions of the heart based upon the above-described principles of the $\Delta$V-pump in order to make it possible to enhance the methods of analyses, diagnosis and therapy of the heart. The heart is modelled by a computer-based representation of one dynamic displacement pump or of two interconnected dynamic displacement pumps, $\Delta$V-pumps.

Many different requirements, boundary conditions, must generally be met when implementing a mathematical model on to a pump, describing its construction, power source, pumping and regulating functions in a circulatory system. There will be even more boundary conditions if the circulatory system comprises two circulatory systems, as is the case with the heart, and pumps, where the flow to and from the two circulatory systems always shall be in balance.

Usually individual's heart and circulatory system are investigated at rest when flow, frequencies and inotropic stimuli are low. Most of all reference values telling if the heart and the circulatory system is in a good or bad position are found and compared during idling pumping motions of the heart. During these circumstances the energy to mechanical converting, characteristics of the DeltaV-principles are less pronounced for the pumping, filling and regulating functions of the heart. This may be one of the reasons why the squeezing pumping functions of the heart together with the regulating functions of the "Frank-Starling law" as a lost motion squeezing displacement pump, still exists as a platform for heart and circulatory diagnostics of today.

New investigating methods like MRI (Magnetic Resonance Imaging) and Spin CT (Spinning Computer aided Tomography), and further developments within the ultra sound technique with TVI (Tissue Velocity Imaging) and reflector based velocity imaging (2D strain) with reduced visualization of false movements, is showing that the heart is pumping with longitudinal motions of an AV (Atria-Ventricular)-plane together with squeezing motions of the muscles. The AV-plane is defined as the orifice of the mitral ring at the left ventricle and correspondingly the orifice of the tricuspid valve will serve as an AV-plane for the right ventricle. The functions of the right ventricle are very seldom discussed. The true area of the spherical piston and the DeltaV-functions are not yet understood, even though heavy discussions have started to explain what kind of forces there are acting on the ventricular filling. Terms like Diastolic heart failure have become a popular scientific discussion subject. What gives the heart its regulating functions within the new insight of a piston like pumping function has not yet become a discussion subject.

Investigations of the heart with old or new investigating methods bring a lot of information that may be very hard to interpret. Every mechanical device can be expressed in state diagrams if the mechanics behind the working principles are fully known. That is not the case concerning the heart as a mechanical device. The filling and regulating functions of the heart has been debated during centuries. The complex architecture and motions of the heart together with unknown mechanics, makes it almost impossible to determine the contributions of different activities and functions within the heart even at very low flow and heart rates. At higher flow and heart rates, all investigating methods, more or less, shows a chaotic output of information. This, together with the general belief that the heart is pumping with squeezing functions, are probably the reasons why activities of the heart muscle cells have been in focus in trying to understand and analyze the functions of the heart.

The general object of the present invention is to create a system that by processing means in various kinds of investigating methods can be used in one, two or three dimensions to register, analyze, validate, present, simulate and communicate the functions of the heart as a cluster state machine and optionally the circulatory system including the coronary system down to molecular levels This would in a substantial way improve the knowledge about the pumping and regulating functions of the heart and create better and faster diagnostic and therapeutic tools and methods.

SUMMARY OF THE INVENTION

The general object of the present invention is achieved by a state space model in accordance with the independent claims.

Preferred embodiments are set forth by the dependent claims.

According to a first preferred embodiment of the present invention a State Space Model (SSM) of the heart and all its functions is created. The SSM can, by an Input Mean Manager (IMM) related to SSM, handle data from investigating methods of the heart and optionally the circulatory systems. IMM can, by a processing means, separate all the functions of the muscle cells from their volumes, and transfer these data and create incomplete and/or complete wire frames and/or surface mesh models of the heart with impacts of the boundary conditions concerning the model and optionally the circulatory system. These data and other data can by a Heart State Analyzer be presented as interacting data as e.g. discrete and/or dynamic state diagrams, optionally handled and organized by an Interconnecting Management System (IMS).

The output from SSM is analyzed by a Heart State Analyzer (HSA) that can present these related data as e.g. discrete and/or dynamic state diagrams, optionally handled and organized by an Interconnecting Management System (IMS).

According to a second preferred embodiment of the present invention a Heart State Validator (HSV) module according to SSM preferably managed by IMS is created. All modules in SSM are interacting to generate the pumping and regulating functions of the heart and optionally the circulatory systems. There are many possibilities by comparison and calculations to create control data that manually and/or automatically can validate the data that are stored to present all the functions of the heart and optionally the circulatory systems.

According to a third preferred embodiment of the present invention a Graphical User Interface (GUI) module is created that graphically can present one or several interacting discrete and dynamic time related state diagrams describing the pumping and regulating functions of the heart, and optionally the circulatory system, down to molecular levels according to SSM and preferably managed by IMS According to a fourth preferred embodiment of the present invention an Efficiency Rate Analyzer (ERA) module is created that by comparing the outcome of the mechanical functions of the heart with the heart muscular rearrangements according to SSM, preferably managed by IMS, can be used to calculate and optionally enhance the efficient rate of the muscles as construction material and power source.

According to a fifth preferred embodiment of the present invention a Heart State Simulator (HSS) is created, and optionally the circulatory system including the coronary system (FIG. 2) according to SSM preferably managed by IMS. This simulator can be used for learning purposes and simulate the impacts that different kinds of boundary conditions changes will have on the modules of SSM.

According to a sixth preferred embodiment of the present invention a database according to SSM preferably managed by IMS is created. In a further process, artificial intelligence (AI) systems according to SSM can be created.

According to a seventh preferred embodiment of the present invention simple investigating devices are created, like pressure sensors, microphones, photo sensors, oxymeters etc that, equipped with HSA and GUI according to SSM preferably handled by IMS, can create discrete and/or dynamic time related state diagrams, to be used both inside and outside the body that manually and/or automatically, e.g. by telemedicine, can serve as control devices for the heart and optionally the circulatory system of an individual.

According to an eighth embodiment of the present invention, SSM is used to find the functions of the heart by dynamic triangular measurements calculated by HSA. This mapping of the active contours in one, two and/or three dimensions may then be used to create wire frames and/or surface mesh models of the heart, or parts of the heart.

According to a ninth preferred embodiment of the present invention a simple and fast method is created that describes the interactions of the pumping and regulating functions of the heart.

By using SSM it will be much easier to see and understand when, where, why and how different external and/or internal parameters change the pumping and regulating functions of the heart. This can be very useful in learning processes and especially to study and analyze the earlier unknown regulating functions of the heart.

SSM is further very suitable to be used for e.g. processing, presentations and simulations of the heart and its functions in the circulatory systems with parameter changes down to chemical and micro conducting levels of the heart muscle cells and other cells and functions related to the circulatory systems.

The databases can manually and/or automatically be used as support for e.g. analyzes, processing, presentations, simulations, diagnosis, prognosis, medical and surgical treatments.

In this way, even rough, simple and quick investigating methods like external flow, pressure and sound monitoring may be used to determine the heart functions. This makes SSM suitable as software and optionally hardware in home-care devices for e.g. on-line communications and investigations of an individual's circulatory system as e.g. a follow up of medical treatments, health-care and training.

Thus, the general object of the present invention is achieved by creating a system that by processing means in various kinds of investigating methods can be used in one, two or three dimensions to register, analyze, validate, present, simulate and communicate the functions of the heart as a cluster state machine and optionally the circulatory system including the coronary system down to molecular levels This is achieved by creating a State Space Model (SSM) of the heart and all its functions, analyzed by a Heart State Analyzer (HSA) as discrete and/or dynamic time related state diagrams, handled and organized by optionally an Interconnecting Management System (IMS).

SSM is related to boundary conditions of:
the surrounding areas, the muscle cells way of functions, the DeltaV-pump functions, the interaction of Intra Ventricular Septum (IVS) and flow, pressure, pressure gradients into and out of, inside and outside the heart.

Together with additional modules as Heart State Validator (HSV), Heart State Simulator (HSS), Graphical User Interface (GUI), Efficient Rate Analyzer (ERA) module and reference database according to SSM, the interconnecting management system (IMS) can be used for e.g. registrations, validations, communications, database management, analysis, processing, presentations and simulations to improve knowledge, diagnostics and therapies.

Except of being used by professions SSM are very suitable in home care devices such as pulse, sound and pressure monitors for e.g. on line communications of an individual's circulatory system. These can e.g. be used for follow up studies of medical treatments, health care and training.

SSM can further manually and or automatically e.g. support registration, analyzing calculating and modelling modules with data from, databases to enhance the information's and create more reliable investigating methods.

By knowing the true pumping and regulating functions of the heart the inventors have now found out that new, more effective, less time consuming investigating-, analyzing-, simulating- and presentation-methods can be used to create more effective diagnoses prognoses, treatments, communications and database handling can be created. This is basicly done by creating the so-called State Space Model (SSM) of the heart that in interacting modules separates the masses of the muscle cells functions to focus on the constructions, pumping and regulating functions of the heart in relation to changes in boundary conditions as e.g. muscle cell functions, the surrounding areas, pressure, pressure gradients and flow, both in to, inside and out of the heart including the coronary circulatory system. The model relies on a mathematical model of the human heart. The model is of limited complexity but still it catches the mechanical pumping and regulating functions of the heart. This creates many beneficial properties compared to other approaches ("black box"-models, models that involve finite elements etc.). The model can be expected to show strong performance when interpolating between known observations as well as when extrapolating outside the space of known observations. Deploying the model in calculations involve limited computer resources and calculation results can be obtained more or less momentarily.

With this model it will be possible to focus the investigating methods, registration and analyzing systems etc. on the final results of the pumping and regulating functions, and not as today, having the focus on the activities of the muscle cells in trying to understand and present the functions of the heart.

The regulating functions of the heart are of special interest since failing regulating functions renders in pulmonary hypertension dyspnoea, pulmonary oedema, great discomfort and death. Decreasing pumping functions results in decreasing minute volume and thus reduces the physical working capacity of the individual with usually no discomfort and death. Compare the heart of a child, a normal individual and a well trained sportsman. In a healthy condition they have the same regulating functions but they all have different pumping capacities.

According to a preferred embodiment of the invention the State Space Model (SSM) may be incorporated in an interconnecting system, herein referred to as the Interconnecting Management System (IMS) to serve as an extensive framework and make related connections between various kinds of information about the heart and the circulatory system. IMS optionally handling SSM may be used in different kinds of investigation methods, devices and in databases to register, analyze, calculate, simulate, display and communicate the hearts functions as separated interactive layers.

Since IMS, by including SSM, is related to the both the constructions and functions of the heart muscle cells it can relate and present all knowledge, computer modelling etc. of the heart muscle cell to the construction, pumping and regulating functions of the heart.

IMS can also, as a managing device, satisfy the boundary conditions concerning the whole circulatory system including the coronary system.

Since IMS can focus on the mechanical functions of the heart, fast and less complex investigating methods and analyzing system can be used to evaluate and present the pumping and regulating functions of the heart. This makes IMS very suitable in home care devices as e.g. on line communications of an individual's circulatory system.

SHORT DESCRIPTIONS OF THE APPENDED FIGURES

The present invention will now be described in detail with references to the appended figures.

FIG. 1a and 1b schematically illustrates the principles of a ΔV-pump.

Figure 7A:
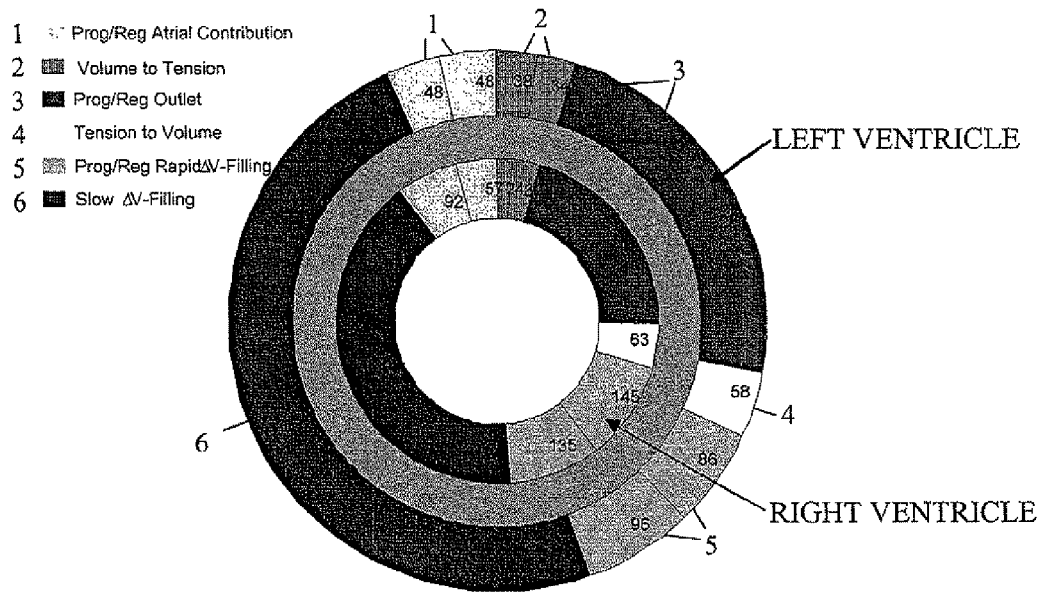

FIG. 7A is an example of a discrete time related state diagram achieved in accordance with present invention by an ultra sound registration of a normal functioning heart just showing discrete time related events obtained e.g. by velocity changes in two points, one in the medial part of the DeltaV-piston of the Right Ventricle (RV) and the other point in the lateral part of the DeltaV-piston of the Left Ventricle (LV).

Figure 7B:
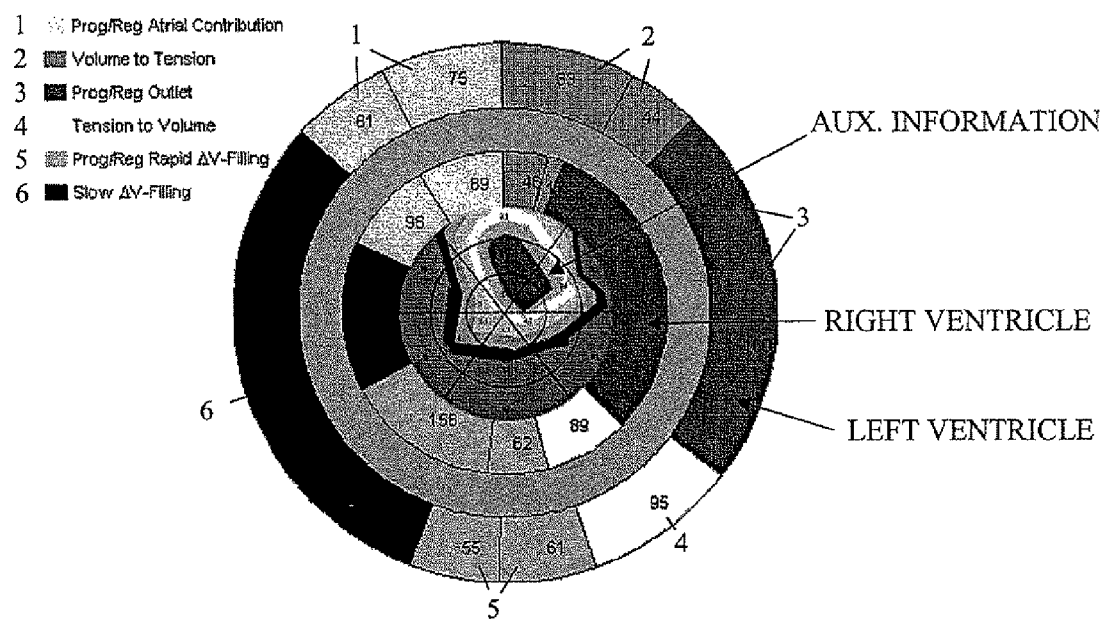

FIG. 7B is an example of a discrete time related state diagram achieved in accordance with present invention by an ultrasound registration of a pathological functioning heart achieved as in FIG. 7A with an added picture displayed as a "Bulls eye" in the centre prepared to show dysfunctions in the rearrangements of the muscle masses to give further information behind the changed mechanical functions.

Figure 8:
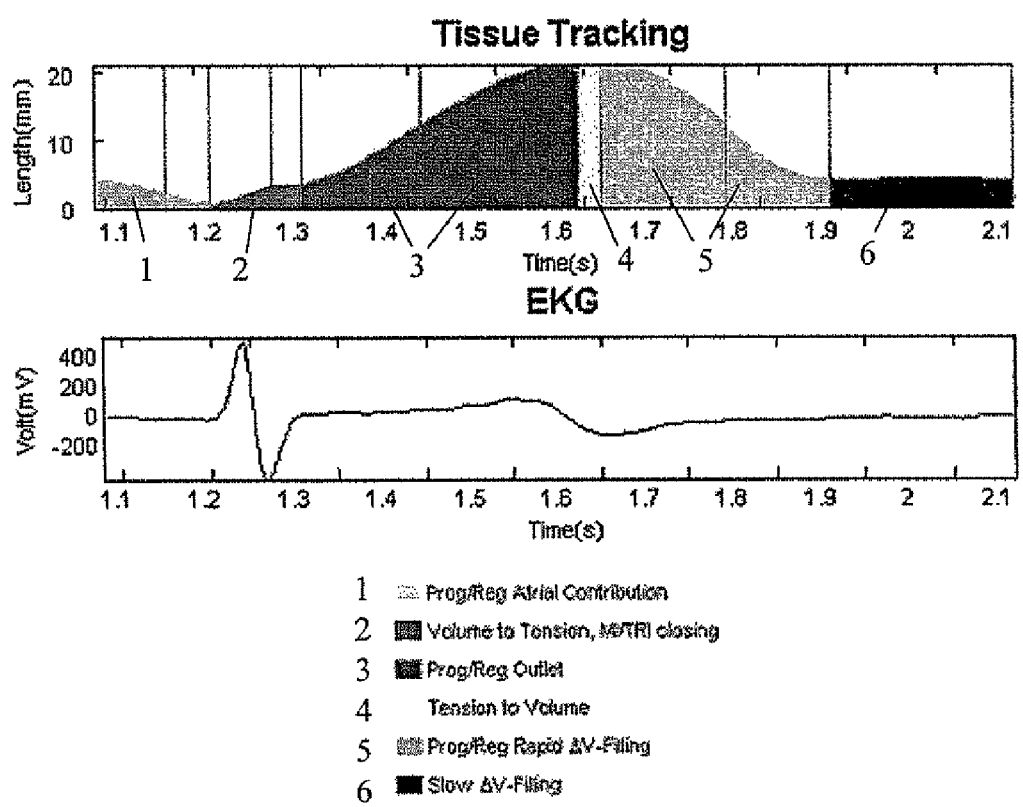

FIG. 8 is an example of a dynamic time related state diagram achieved in accordance with present invention by an ultra sound registration showing the motion at one point of the DeltaV-piston located in the lateral part of the Left Ventricle (LV).

Figure 9:
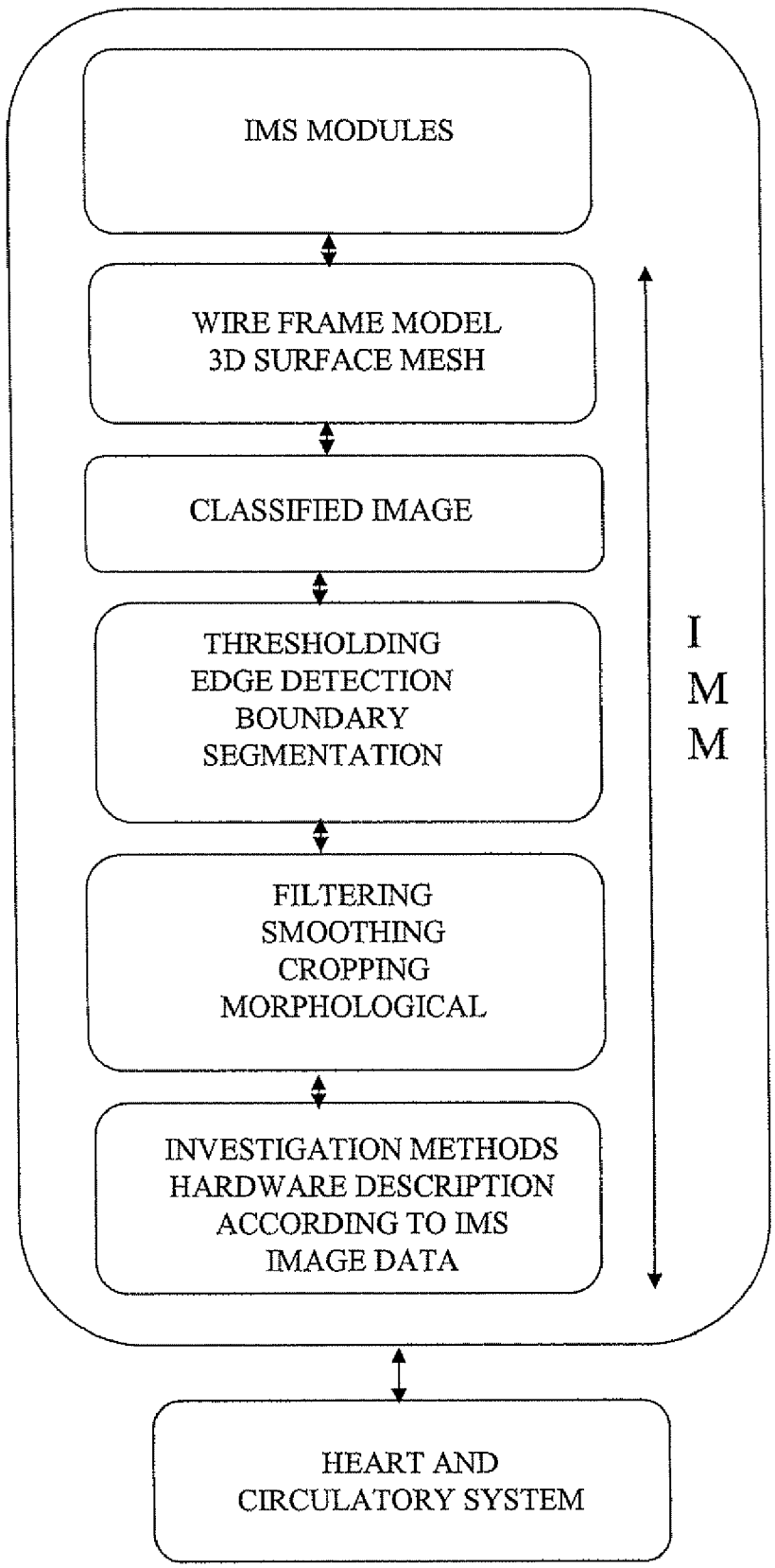

FIG. 9 schematically illustrates, as an example of programming steps, how to implement SSM in an imaging device unit able to register e.g. 2D, 3D geometry, volume, and regulating functions in relation to internal and external changes.

Figure 10:
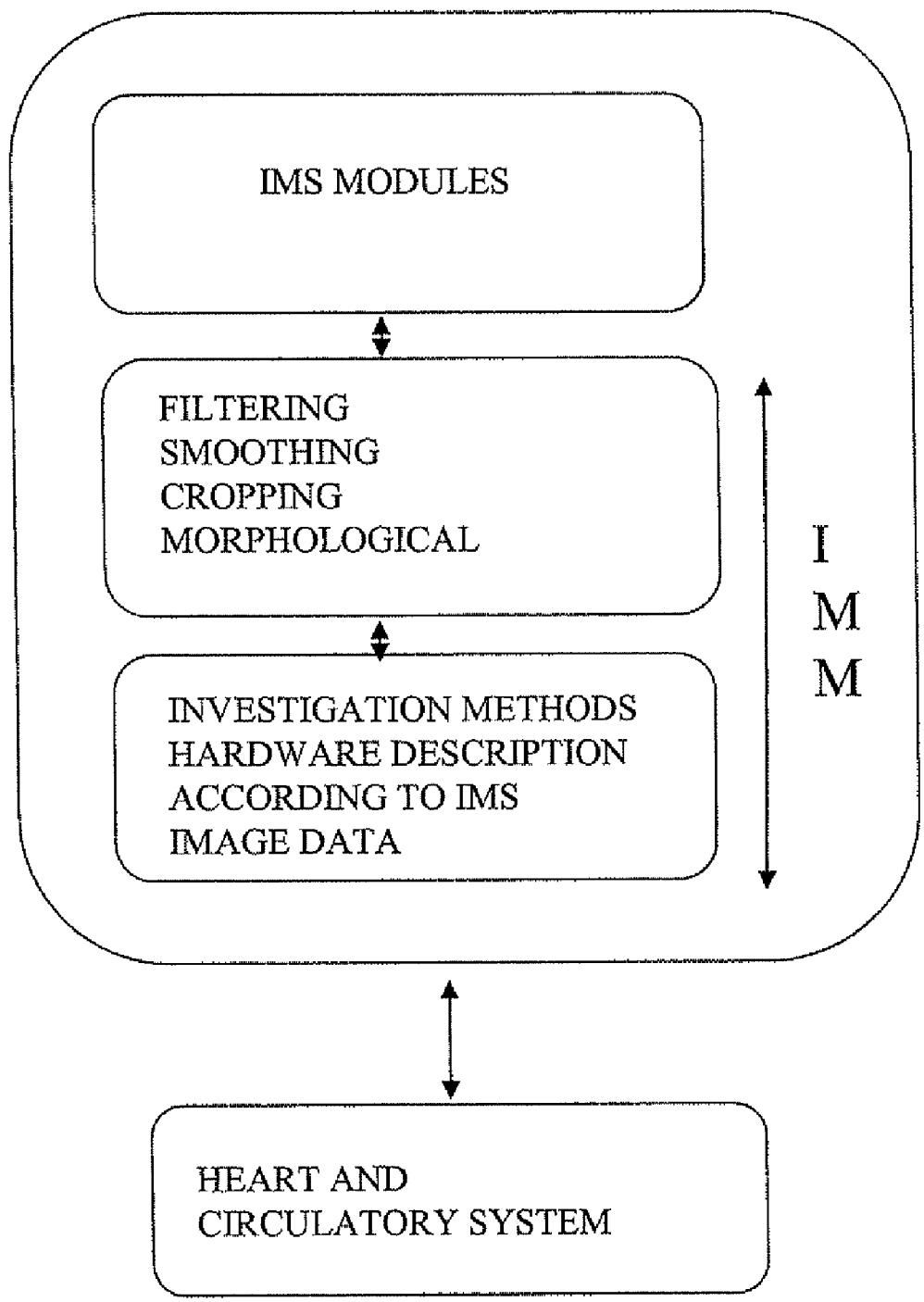

FIG. 10 schematically illustrates as an example of programming steps how to implement SSM in a blood pressure monitoring device.

DETAILED DESCRIPTION OF PREFERRED
EMBODIMENTS OF THE INVENTION

In order to fully describe all aspects of the present invention it is considered necessary to include, in the following, parts of the detailed description of the above-identified PCT-application (PCT/SE2006/000114).

The key to reproduce the heart and its functions is to define the fundamental boundary conditions that Nature has been able to fulfill, creating the pumping and regulating functions of the heart.

Figure 3:
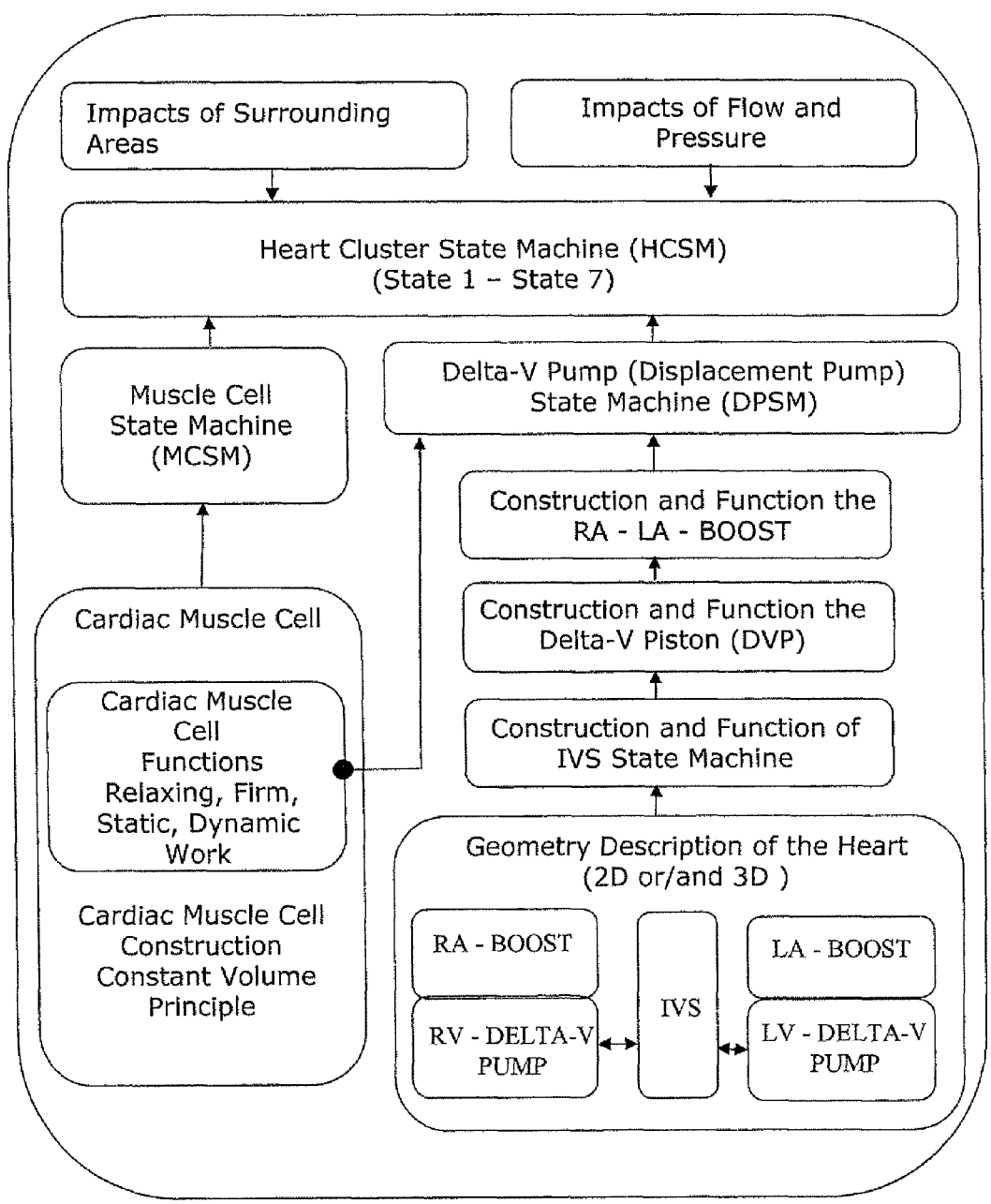
FIG. 3 illustrates an architecture of a State Space Model (SSM) illustrating a separation of the heart as a cluster state machine into interactive modules according to the first preferred embodiment of the present invention.

According to the underlying principles behind the present invention this is achieved by transforming the heart in technical terms to a heart cluster state machine running with the dynamic boundary conditions that normally are set by Nature. The heart cluster state machine is a result of fusions of dynamic boundary conditions of finite heart muscle cell state machines to a muscular syncytium the heart muscle, adapted to the dynamic boundary conditions of a $\Delta$V-pump state machine (FIG. 3). This creates the heart cluster state machine that will follow the dynamic boundary conditions of said finite heart muscle cell state machine and of said $\Delta$V-pump state machine.

The working conditions of the heart cluster state machine will be equal to the working conditions of the heart inside a body and may be expressed by using generally available computing, imaging, storage, and analysing systems.

As briefly discussed above, instead of pumping with squeezing functions being the traditional pumping movement of the heart, the present invention is based upon the observations that the heart is pumping with back and forth going movements with a piston-like unit, referred to as the Delta ($\Delta$) V-piston or the spherical AV-piston. The area of the piston consists of a more flat area and a curved area. The flat area consists of the ring of annulus fibrosis, the AV-ring, and its four valves which means that it includes the connection areas of aorta and the pulmonary artery T. Pulmonalis.

The curved area being convex in two-dimensional imaging or spherical in three-dimensional imaging consists of the left and right muscles connected to the flat area, the ring of annulus fibrosis.

When the $\Delta$V-piston is drawn towards the apex of the heart and forces the blood contained in the ventricles into the pulmonary and systemic circulation, it will at the same time draw blood into the atria and its auricles as a consequence of the boundary conditions of the AV heart pump and its surrounding areas. The convex parts, areas, of the $\Delta$V-piston that are in direct contact with the pericardia including the projected areas of Aorta and Pulmonalis that are in direct contact with the surrounding tissues will form the direct $\Delta$V volumes. The areas of the $\Delta$V-piston that are in indirect contact with the surrounding volumes will form the indirect $\Delta$V-volumes. Such areas are mostly covered by the auricles and to a certain extent T. Pulmonale and Aorta.

During the beginning of ventricular diastole, during the phase when the ventricular muscles start to be relaxed, the $\Delta$V-piston starts to return to its initial position by filling up the $\Delta$V volumes it generated during the contraction of the ventricles. That is done under influence of dynamic and static forces of the masses and by stored energy in the heart structures and its surrounding areas, created by the downward movement of the $\Delta$V-piston during ventricular systole. Pressure gradients over the $\Delta$V areas generate a hydraulic return of the $\Delta$V-piston, and this is referred to as the $\Delta$V-function.

Most of the outer volume changes are the direct and indirect $\Delta$V volumes in connection to the motion of the $\Delta$V-piston and in the areas of the resilient suspension at the apical-diaphragm part of the heart. The abilities (as described in the cited theses) of the heart to change the relative volumetric capacities of the right and left ventricles are mainly done by motions of the common ventricular wall, the Intra Ventricular Septum (IVS). During ventricular diastole the relaxed state of the muscles the IVS can adapt its form and position depending of the pressure gradients between the two ventricles. During ventricular systole the ventricular septum together with the rest of the left ventricular heart muscle assumes an essentially cross circular cross-sectional configuration and takes a distinct position independently of its shape and position during diastole. This is so, because during ventricular systole the pressure in the left ventricle is always higher than the pressure in the right ventricle. If the configuration and position of the ventricular septum during diastole, the relaxed state, are different from the configuration and position during systole, the active state, the ventricular septum, acting like a diaphragm pump, therefore provides an increased stroke volume for one ventricle and a correspondingly reduced stroke volume for the other ventricle. In this way, the ventricular septum accomplishes a double-acting regulation to maintain the balance between the two branches of the circulatory system (the pulmonary circulation and the systemic circulation).

The dynamic boundary conditions needed to describe the heart as a heart cluster state machine are clarified by giving examples of subdivided boundary conditions for the working principles of the muscle cell and subdivided boundary conditions for the working principles of the heart being a $\Delta$V pump state machine.

I The dynamic boundary conditions of a muscle cell as being a finite state machine, can be subdivided in boundary conditions and working principles as follows:

Ia the boundary conditions of chemical, electrical and mechanical ways of creating power and triggering the finite muscle state machines being parts of a conduction system in order to, in synchronized ways, achieve optimal order for the pumping- and regulating functions of the heart.

Ib the boundary condition of a connective tissue network around the muscle cells allowing firm constructions, elongating and shortening with enough space for the muscles being thicker at the muscular contraction.

Ic the boundary conditions of arranging muscle cells to create a four-chamber volume pump acting like a $\Delta$V-pump but serving to circulatory systems keeping them in an exact balance. Naturally, two and three chamber hearts will have other conditions.

II The dynamic boundary conditions of the heart working as a $\Delta$V-pump state machine are subdivided in boundary conditions and working principles as:

IIa The boundary conditions of surrounding tissues encapsulating a four-chamber volume with in- and outlets having functions and properties supporting the $\Delta$V functions of the heart.

IIb. The boundary conditions of a movable $\Delta$V-piston, having valves, and outlet vessels, dividing an inner continuous volume of the heart into supplying and expelling volumes and also generating ΔV-volumes arranged to create ΔV-functions.

Figure 1A:
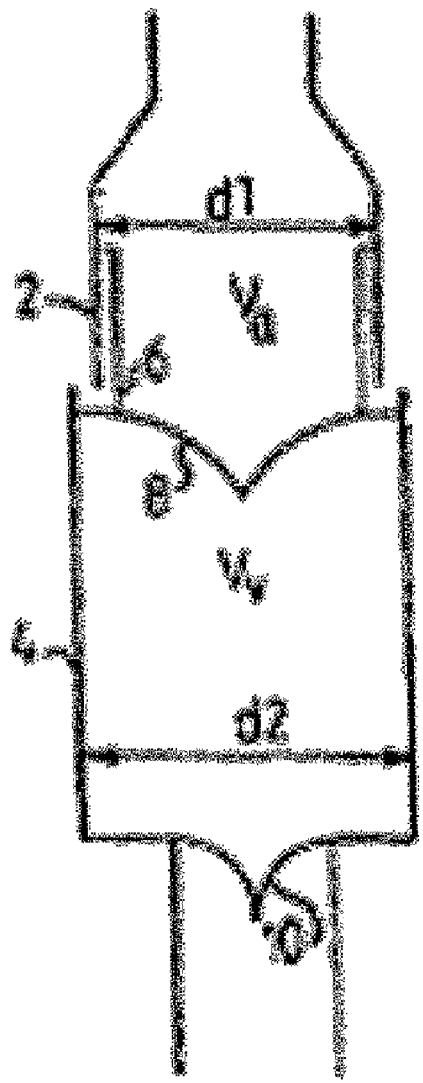
Figure 1B:
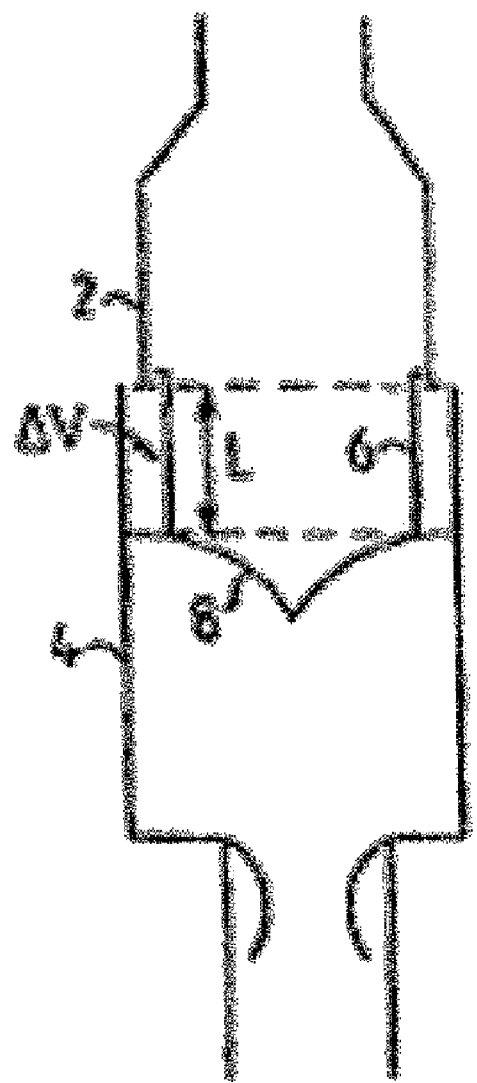
Figure 2:
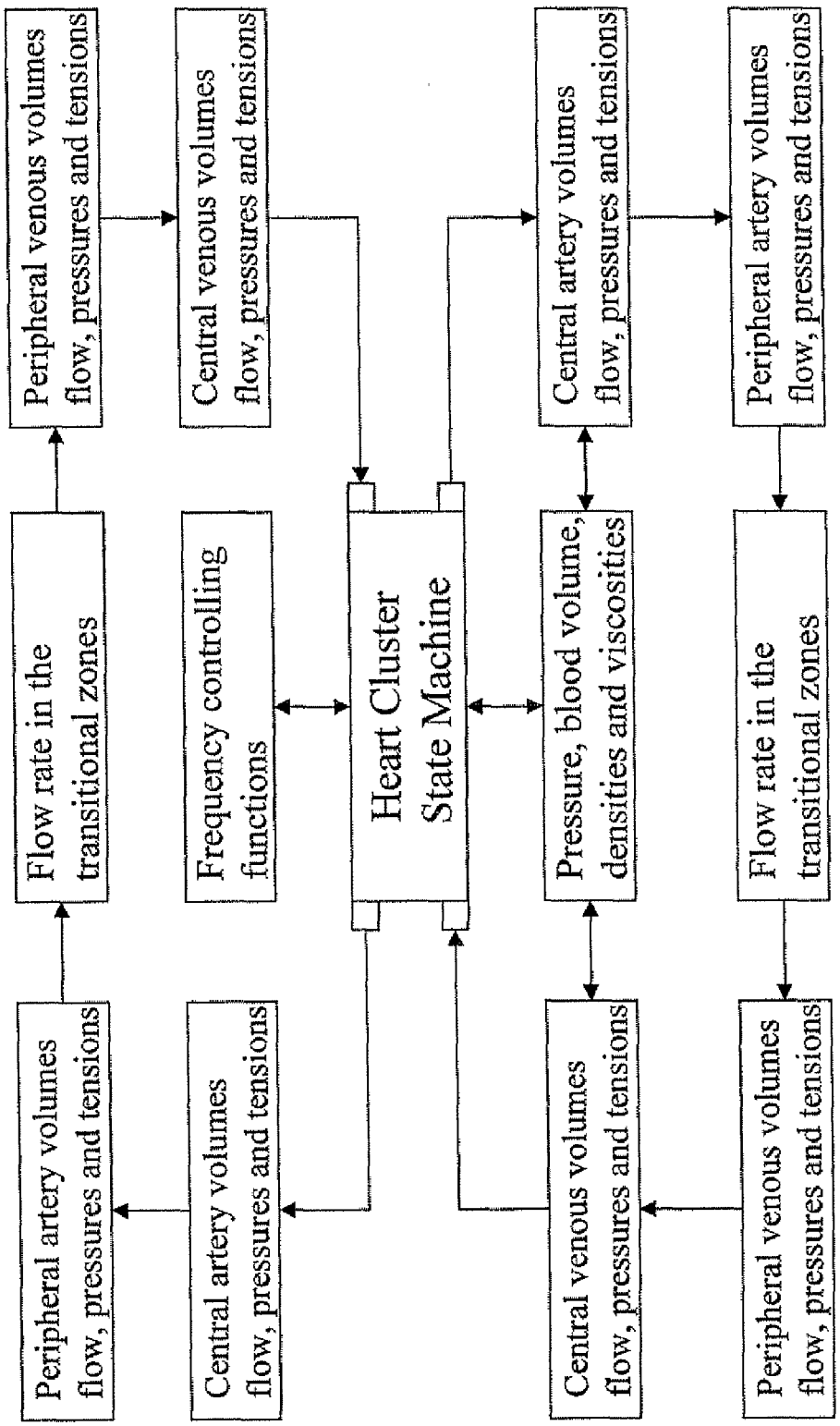
FIG. 2 illustrates in accordance to the present invention an example of a model of a human circulatory system according to SSM.

In traditional circulatory systems with ordinary pumps it is usually the speed of the pumps that controls both the inflow and outflow. That is not the case with the Dynamic Displacement pumps, the ΔV-pumps. They are inherently controlled by the inflow. The ΔV-volumes create ΔV-functions that determine the stroke length and in case of the heart also determine the sizes of the heart as a ΔV-pump. This means that the ΔV heart pump has to be incorporated in a circulatory system to show or create its true pumping and regulating functions. In this way the dynamic boundary conditions controlling the venous return will have a very important role in controlling the cardiac output. The ΔV heart pump will, if the frequency and power are high enough, always try to pump away the blood that is coming through its inlet vessels. This has earlier not been fully understood. The main dynamic boundary conditions of circulatory system that are needed to support or being supported by the ΔV-heart pump can be described according to FIG. 2 as:

III Dynamic boundary conditions of the central venous volumes (e.g. pressure, flow, volumes, tensions of the larger veins including the pulmonary veins leading to the heart).

IV Dynamic boundary conditions of the peripheral venous volumes (e.g. the blood volume exchange and storage capacity of capacitance vessels).

V Dynamic boundary conditions of the central arterial volumes (e.g. pressure, flow, volumes, tensions of the larger arteries including the pulmonary arteries leaving the heart).

VI Dynamic boundary conditions of the peripheral arterial volumes (e.g. the variations of blood volumes needed to support different organs at different times and activity's controlling the flow rate in the transitional zones, and pressure drop to values of the venous pressures).

VII Dynamic boundary conditions of keeping the total blood volume, blood densities, viscosities, shearings etc.

VIII Dynamic boundary conditions of controlling heart rates and blood pressures.

With the heart presented as a ΔV heart pump it will be possible to modulate and simulate the natural circulatory system. The synergies between the functions of the heart and the functions of the circulatory systems will be better understood and will increase the demands of having answers to the questions when, where, how and why the heart does perform as it does. It will for example be very useful in medical treatments, intensive care and research.

In other words, each muscle cell must be arranged/configured such that it both fulfils the conditions for its own working regimen and also fulfils the requirements as a part of the structure building up the heart as a ΔV-pump. The working regimen creating power by shortening and thickening and the boundary conditions behind that are well known.

All experimental working models of the heart have under all circumstances been described with squeezing functions. This was obviously the case when the heart was supposed to do its pumping and regulating functions by external squeezing motions of the atria and ventricles in a rhythmic counter acting way.

With the new Magnetic Resonance Imaging technique (MRI) the opinion among leading researchers for the fourth time in history adopt the idea that the heart is pumping with piston like motions of the AV-plane together with squeezing motions of the muscles. The AV-plane is defined as the orifice of the mitral ring at the left ventricle and correspondingly the orifice of the tricuspid valve at the right ventricle. The functions of the right ventricle are very seldom discussed.

The muscle cells way of working by shortening and thickening will generate problems once closed volumes as in the heart are made. The muscular cell volumes remain constant during its working states. This means that every working muscle cell because its thickening will have an impact on its neighbor cells and so forth. The volume geometry in the short axis view of the whole heart and the left ventricle in particular is more or less circular in shape. It means especially if the heart should do its pumping functions by squeezing pumping functions that every muscle cell have to interact in pushing, pulling and rearranging itself and neighbor cells in all directions on its way and thickening towards the center.

Nature has created a large spherical DeltaV-piston. This piston starts far below the AV-ring where the conical parts of the ventricular outer contours proceed to a spherical form that finally is attached to the AV-ring. This formed spherical area is to a large extent covered by the auricles and their edges and generates together with the outflow tract of the Aorta and T. Pulmonalis the DeltaV-piston. The large area of the DeltaV-piston reduces the need for a long stroke length, reduces muscular obstructions to flow and creates DeltaV-volumes.

Organized muscle cells in a longitudinal clockwise outer "layer" and an inner longitudinal counterclockwise "layer" form an X orientation, with a reinforcement circular oriented "layer" in between. Together with a complex network of trabeculae, these oriented muscle cells generates longitudinal motions and narrowing that can follow the outer contour set by the pericardial sac and its surroundings.

The muscles way of working by shortening and thickening will become a matter of packing and unpacking in a proper physiologic order. The thicker the muscular wall has to be the harder it will be to solve these tasks and finally the muscles will be an obstacle for the pumping and regulating functions of the heart.

The muscle cells do not substantially change their volumes during static or dynamic work. This means that the volumes generated by the atria, auricles or the ventricles always will contain constant muscle volumes. In the construction of the heart as a DeltaV-pump there are needs of both relaxant and firm properties of the construction material as well as needs of power resources. The muscle cells way of working can, with support of the hearts surroundings and pressure gradients, satisfy these needs.

Detailed Description of FIG. 3, Illustrating the Architecture of the State Space Model (SSM), Wherein by Using the Deltav-Pump as Displacement Pump all Controlling Requirements of the Heart have been Fulfilled:

The heart as a cluster state machine, described by a logic state diagram (S1-S7, see FIG. 6), can be subdivided in two major lines of interacting modules as interacting modules in a State Space Model (SSM). The interacting machines, the finite heart muscle cell state machines and DeltaV-pump state machines are separated.

The first column (FIG. 3) describes the finite heart muscle cell state machines. The column starts with the "Cardiac Muscle Cell Construction" module. This module describes the construction of the muscle cells and their interrelations on molecular and micro levels including micro conduction nutrition and other chemical reactions. The next module "Cardiac Muscle Cell Functions" in this line describes the cardiac muscle cell functions as construction material with possibilities to be reluctant by elongation, firm by static work and create dynamic work by shortening. This module also includes the conducting system. The third and final module in this line is the "Muscle Cell State Machine" that includes the muscle cell with all its masses and functions. The module takes care of the facts that a muscle cell has a substantially constant volume during all its states and thus by elongation becoming thinner and by shortening becoming thicker. This means that this module takes care of the architecture of the heart in order to take care of the rearrangements of the muscle masses during its working states.

The second column describes the DeltaV-Pump State Machine. It starts with the main module divided into sub modules that schematically are showing the construction of the heart as a geometric description of the heart in 2D or/and 3D. The heart as a mechanical device is made by a fusion of two DeltaV-pump state machines creating the right and left hand side of the heart. The Right and Left Ventricle, RV and LV, are the outlet volumes while RA and LA made by the Right and Left Atria and Auricles are the inlet volumes. The right and left hand side of the heart are together creating a third DeltaV-pump, the total heart.

The second module in the second column describes the constructions and functions of Intra Ventricular Septum (IVS) as a result of the fusion of the two DeltaV-pump state machines generating the third DeltaV-pump state machine. In a mechanical point of view IVS separates the outlet volumes, RV and LV, from each other. The inflow volumes RA and LA are separated by the outflow tract of Pulmonalis and Aorta together with the intra atria septum, mostly a small membrane of foramen Ovale. The interacting motions of the IVS, shown by the arrows in the main module and in FIG. 4D, will have great impacts on the pumping and regulating functions of the heart. The functions of IVS will in detail be described below.

The line dividing the inlet volumes and the outlet area of Pulmonalis and Aorta from RV and LV formats the DeltaV-piston. Its constructions and functions are described in the third module in the second column. The connections of the ventricular volumes to Annulus fibrosis that holds all four valves are spherical in shape. That makes the DeltaV-piston to have a spherical shape made by the outer contours of the muscle cell volumes. This area is very large but also to a large extent covered by the atria and auricles. This arrangement broadens the piston area towards the inlet volumes and decreases the areas forming the DeltaV-volumes. These arrangements are also very suitable as booster arrangements to increase the stroke length of the DeltaV-piston by atria and auricular contractions, "RA- and LA-Boost"

The fourth module describes the construction and functions of the right and left atria and auricle constructions. Their constructions and functions are in detail described in the presentation of a logical discrete time related state diagram below.

The fourth module ends up in the fifth module "DeltaV-Pump State Machine". This module consists of lines, wire frames and/or surface mesh of outer contours and optionally the inner contours of the muscle volumes in 1D to 3D. The lines and wire frames and/or surface mesh have no muscle volumes but can optionally enclose the muscle volumes. These lines, wire frames or surface mesh are supposed to have the same functions as the cardiac muscle cells and classified as active contours. This transformation is shown by the arrow pointing from the module "Cardiac Muscle Cell Functions" to the "DeltaV-Pump State Machine". This operation can be done because the facts that the heart muscle cells do not substantially change their volumes during passive, static or dynamic work. This means in reality that the module "Delta-V Pump State Machine" is achieved from the module "Heart Cluster State Machine" by reducing the muscle cell volumes to zero. In this way the mechanics of the heart will be in focus during the investigations of the heart. The constant volume and rearrangements of the muscle masses, the Heart Cluster State Machine module, can be used to create checking values especially when volume displacements inside and outside, in to and out of the heart are the objects to be investigated and analyzed. Furthermore, the patterns of the rearrangement can be used together with the mechanical functions to simulate, validate, and calculate the performances of the heart.

Other mechanical interactions with the heart as a Cluster State Machine are the "Impacts of Surrounding Areas" and "Impacts of Flow and Pressure". These two modules will more or less constantly change the external and internal geometries of the heart. Under normal circumstances these modules will, together with the DeltaV-functions of the DeltaV-piston, interact in balancing the input and output of the heart to maintain a perfect balance of flow and pressure between the pulmonary- and main circulatory system.

Detailed Description of FIG. 4A-4D:

In order to understand the impacts of the surrounding areas to the pumping and regulating functions of the heart, a model of a Heart Cluster State machine (FIG. 4A) and models of the DeltaV-Pump State Machines (FIG. 4B-4D) have been created.

Figure 4A:
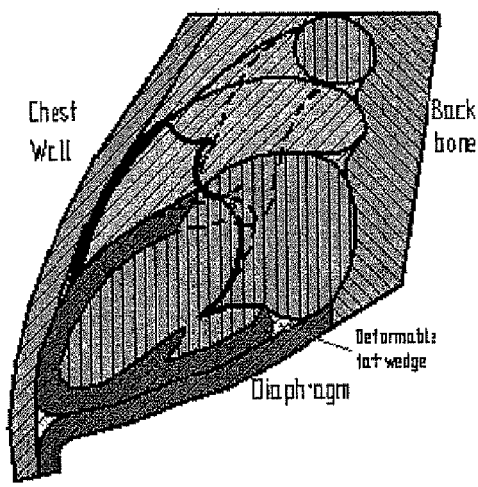
FIG. 4A-4D illustrates an example of a 2D-wireframe model of a heart, achieved in accordance with the present invention.

FIG. 4A is a schematic topographic picture of a long axes cut through the heart. Note its location between the thoracic cage and the region of the backbone. The auricles with their appendixes smoothens the edges around Aorta and Pulmonalis at the outflow tract.

Figure 4B:
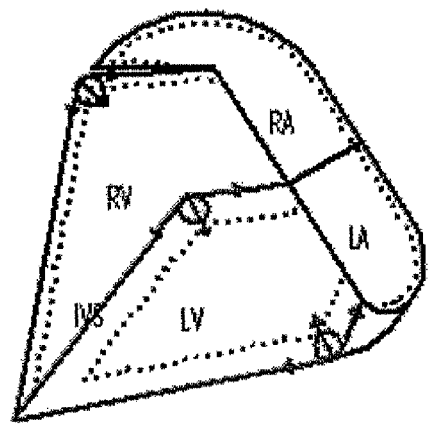

FIG. 4B is a schematic view of the contours of the surfaces that generates the hearts pumping and regulating functions. The outflow and inflow tracts and valves are not shown. The circles are symbols for the first-class levers functions and the easy sliding that the incompressible blood and the slippery surfaces of the epi- and pericardia create. The arrows indicate the common forces, created by the functions of the muscle cells that are needed to balance the hydraulic forces inside the heart. RA and LA stands for Right Atria and Left Atria with the bended parts that corresponds to the auricles and the volume of the deformable fat wedge. RV, LV, and IVS stands for Right Ventricle, Left Ventricle and Inter Ventricular Septum.

Figure 4C:
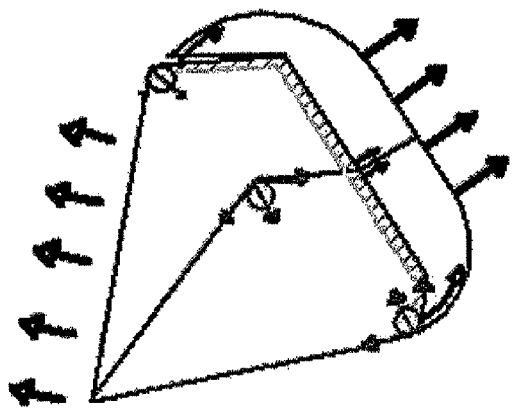

FIG. 4C illustrates the atria contraction that brings the spherical DeltaV-piston to the top of the heart and increases the stroke length of the following ventricular contraction. The large arrows symbolize the strong resistance to motions in these regions.

Figure 4D:
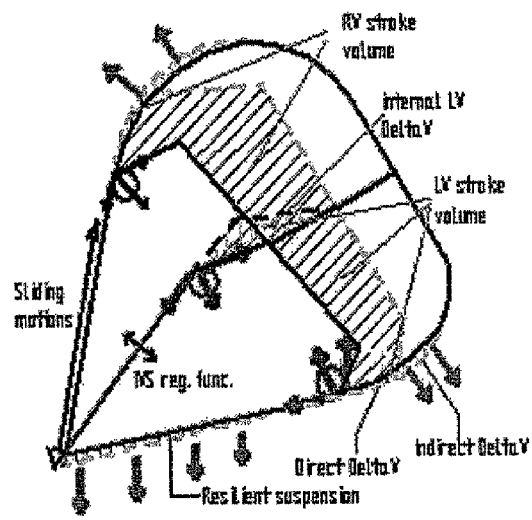

And finally, FIG. 4D demonstrates the piston type pumping function of the DeltaV-piston and demonstrates where to find the volumes that generates the stroke volumes out of the right and left ventricle. Note, that the internal DeltaV-volume "steals" volume from the right ventricle. The areas of the outflow tract are not shown but symbolically included. Note further the sliding motions along the thoracic cage (chest wall), resulting in a resilient suspension at the Apical-diaphragm area generated as a result of the need for counteracting forces to the motions of the DeltaV-piston done by the fixation of the pericardial sac to the diaphragm.

In analyzing FIG. 4A-4D it is obvious to state that the heart has to perform its pumping and or regulating under one or more of these three options:

1. Outer contour changes and thus outer volume changes.
2. Constant outer contours with piston like motions of a piston inside the heart.
3. Constant outer contours with diaphragm pump like motions of the separating wall IVS between the right and left hand sides of the heart rendering in reciprocating volume changes with pumping and/or regulating functions.

Nature has according to SSM in FIG. 3 and illustrated in FIG. 4A-4D made use of all these possibilities.

By definition the DeltaV-pumps always have areas that by motions of the piston can create external volume changes related to as DeltaV-volumes. The interaction of these volumes with the piston makes the expressions DeltaV-piston and DeltaV-functions.

In a living being, the piston holds four valves and also the outlet vessels, Aorta and Pulmonalis. The whole construction of the heart, including the pericardial sac and vessels, is flexible and has to a certain extent elastic recoiling elements. The surroundings of the heart are also flexible except for the thoracic cage and the spinal cord. The strong attachment of the pericardial sac to the diaphragm muscle and hydraulic attachment to the thoracic wall makes the pericardial sac including the heart free to move in parallel with the thoracic wall during breathing, and have during the pumping action an important function as a resilient suspension keeping the total mass inside the pericardial sac in motion at the end of ventricular contraction. The resilient suspension at Apex will reduce the stroke length of the DeltaV-piston but can together with other recoiling forces, static and dynamic forces, by increasing pressure gradients, power the hydraulic return of the DeltaV-piston by the DeltaV-function. The hydraulic and mechanical attachment of the top of the heart and the inlet vessels to the heart, will see to that this area, opposite to the apical area, will be kept in place, both during atria- and auricle contractions as well as during ventricle contractions.

The fusion of the two DeltaV-pumps RV and LV creates a common wall, the Intra Ventricular Septum (IVS), that will act as a diaphragm pump and serve as a double regulating unit to maintain right flow and pressure over the pulmonary circulatory system. The motions of IVS are of great diagnostic importance in visualizing the status of the hearts pumping and regulating functions.

As discussed above, the muscles way of thickening should, in order to focus on the mechanics of the heart, be considered as constant redistributions of muscle volumes inside enclosed outer contours of a volume. This means that it is primary outer contour motions of IVS that make interacting volume changes between the ventricle volumes. Since usually the systolic and diastolic pressures are higher at the left side of the heart, the left ventricle, including IVS, will have a spherical shape. This results in that the muscular cells are oriented to withstand the pressure gradients towards the right ventricle during the ventricles contractions. This means that the muscle mass of IVS will orient its thickening towards the left ventricular lumen. In other words, it will be the motions of the surface area next to the right ventricular volume that change the volumes between the two ventricles.

The ventricular septum is regarded to have two kinds of motions. One is in parallel with the motions of the diaphragm and does not change the volume inside the left ventricle but to a certain extent the volume of the right ventricle. The other motion of the ventricular septum interacts between the ventricles by increasing the stroke volume at one side while decreasing the stroke volume on the other side. This will under normal functions by IVS result in a very effective double regulating function that will maintain right flow and pressure over the pulmonary circulatory system.

The longitude motion of IVS contributes to a third volume exchange between the right and left ventricles (FIG. 4D). This volume, earlier not known, generated by the spherical connection of the ventricular septum to the AV-ring and also to some extent by the outflow tract of aorta and Pulmonalis, creates internal DeltaV-volumes that belongs to the left DeltaV-pump described under SSM in FIG. 3. This means that the left ventricle, generating the internal DeltaV-volume (FIG. 4D), every beat will "steal" from the stroke volume of the right ventricle, a volume that will be returned during the hydraulic return of the DeltaV-piston.

Atria contraction may be regarded as being a booster unit, generating an increased stroke length to the DeltaV-piston. The piston is to a large area covered with double folded auricles and their sharp muscular edges that can be withdrawn by contraction. This generates instantly a situation where a total vacuum would appear if the surrounding areas would not collapse or if the DeltaV-piston would not be lifted up. The later will occur (FIG. 4C) since an upward motion of the Delta V-piston will just rearrange the blood and muscle volumes, in equal volume displacement above and below the DeltaV-piston. This will result in a minimum of change in speed of all masses inside and outside, to and from the heart. At high flow and heart rates, and thus strong forces behind the DeltaV-function, the atrial contraction, except as a result of the conduction system, will have less effect on the stroke volume. Whereas in heart failure it can have life sustaining effects.

Figure 5:
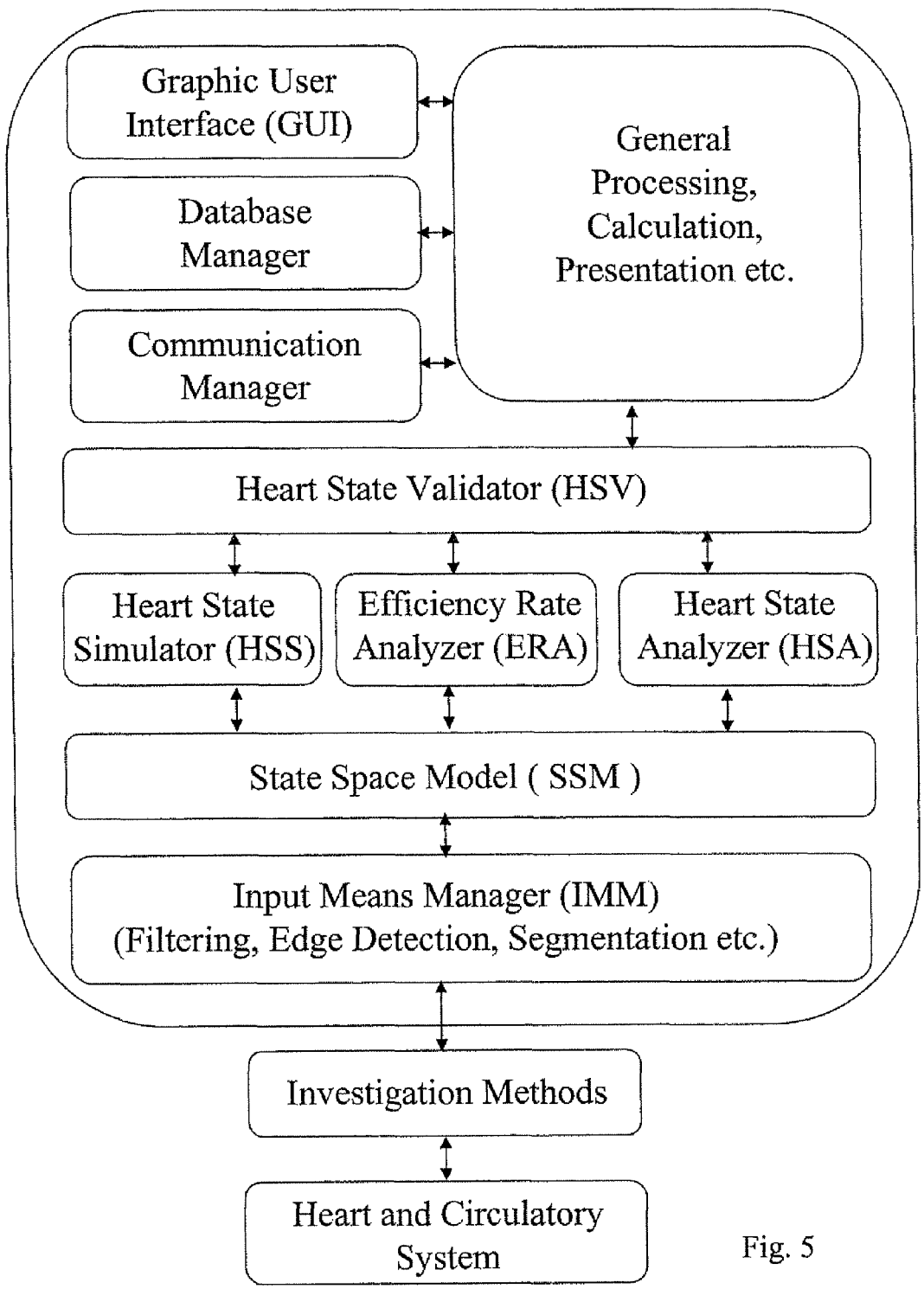
FIG. 5 illustrates the Interconnecting Management System with inherent modules according to preferred embodiments 1-5 of the present invention.

According to present invention SSM has been used as a model to create a Heart State Analyzer (HSA) (FIG. 5). HSA can by software and/or hardware at any point present activity within the modules of SSM as discrete and/or dynamic time related state diagrams. An Input Means Manager (IMM) handles and filters all input data and can in more advanced investigating methods by using e.g. edge detecting algorithms and tissue tracking find the active contours and areas that according to SSM creates the pumping and regulating functions and thus more or less separates the muscle volumes from these active contours and areas. These data can be processed by HSA to create related information's about the functions of the heart. These relations in 1, 2 and/or 3 dimensions can e.g. by dynamic triangular measurements be used to create simple and fast investigating methods, wire frames and/or surface mesh models of the heart or parts of the heart.

The active contours during the whole heart cycle have fairly smooth and known algebraic shapes. The contours of the spherical part of the DeltaV-piston and the contours of the heart walls close to the fixation of the pericardial sack are areas where wrong projections because of motions (wall climbing) makes heavy distortions of important data. These data will further be distorted if the inner contours and thus muscle volume redistributions are measured. Using SSM the distortions of the muscle volume rearrangements can be reduced. Knowing the interactions of the pumping and regulating functions of the heart (FIG. 4A-4D) makes it easier to create mapping points, areas, volumes, triangulations etc. that can be used to separate false motions and activities, from true motions and activities.

This is done by a Heart State Validator (HSV) module. In this way, events, motions, volumes and volume shifts etc can be compared and validated between the different compartments of the heart and to the inflow and outflow including the coronary flow in and out of the heart. Furthermore, the constant muscle volumes and their redistribution motions can be used for further validations and information behind the interacting pumping and regulating functions.

An easy and fast way to get a good opinion about the mechanical pumping and regulating functions of an individuals heart is according to SSM to follow the motions of the DeltaV-piston at the right and left hand side of the heart in relation to the motions of IVS.

In order to control, handle and organize the actions of HSA an Interconnecting Management System (IMS) (FIG. 5) has been created. It can also handle an extensive framework of internal and external modules used for e.g. registrations, validations, communications, database management, analyzes, processing, presentations and simulations.

In this way all boundary conditions of the heart and all its functions can be presented according to SSM.

The actions of HSA can also be described as logic, discrete time related state diagram. Here is an example of such a diagram of the heart according to SSM.

For practical reasons this example will be described as a discrete time-related state diagram concerning only the left ΔV-heart pump. Of course the same events also can be related to the right ΔV-heart pump. The interactions of IVS between these two pumps will anyhow to a certain extent be commented since these interactions are of great importance for the pumping and regulating functions of the heart.

Figure 6:
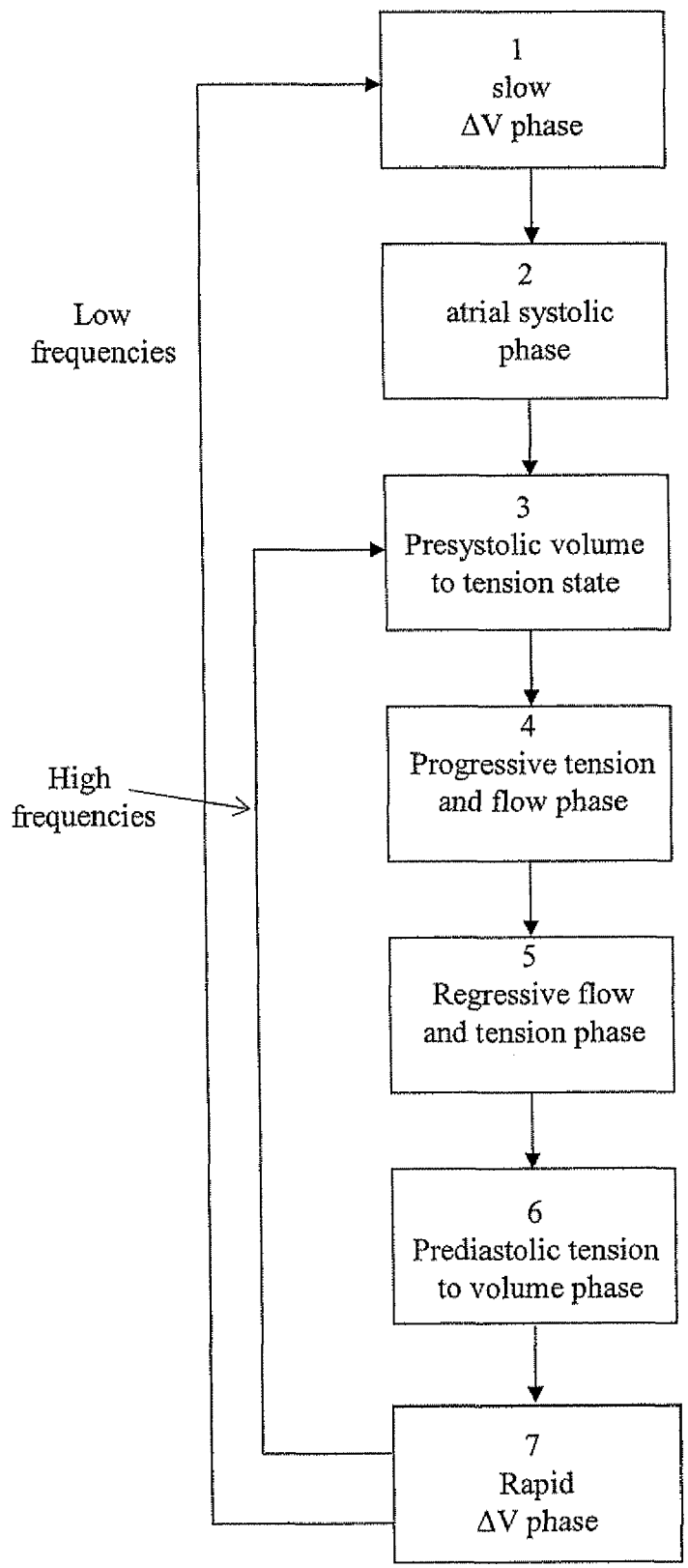
FIG. 6 represents an example of a logical state diagram in accordance with the present invention.

The different states will now be described in detail, especially with references to FIG. 6.

State 1

Slow ΔV Phase.

This phase was earlier referred to as the slow filling phase. But in this context, where the heart works as a ΔV-pump, the "slow ΔV-phase" is more relevant. It is a direct continuation of the rapid ΔV phase, the returning movement of the ΔV-piston. During slow flow and low rates the slow ΔV phase is relatively long.

During this phase the muscle cells of both the atrias and the ventricles, as well as the ventricular septum, are totally relaxed. The left and right halves of the heart may principally be regarded as common volumes inside the pericardium. This results in that the right and left half of the heart, respectively, forms, together with the incoming vessels, compliance volumes. The energy in the incoming flows to the left and right atria result in that the volume of the heart primarily increases in the vicinity where the ΔV-piston moves. This generates energy to the ΔV-functions resulting in that the ΔV-piston changes its shape and position and also generates stretching forces to the ring of annulus fibrosis. The energy in the incoming flows is transferred to both ventricles essentially without being disturbed by the ventricular septum.

The total volume of the heart is depending on the heart frequency and inflow.

The size of the ΔV-pump will be set during this state.

The pericardium and its environment are the main limitations to the possible volume expansion of the heart. During this phase the static forces in the inflowing blood are the most prominent forces. Those surfaces forming the indirect ΔV-volumes (mostly the auricles of the atria) do not contribute during this phase to any net forces to press the ΔV-piston in the direction to the top of the heart. It is mainly the direct ΔV-volumes formed by the enlargements of the heart in connections to the ΔV-piston and the outgoing vessels that performs that action. The egg-like shape of the heart results in that the net forces and the motion of the ΔV-piston towards the top of the heart are limited. The ΔV-piston will enter into a neutral balanced position. This will limit the stroke length of the ΔV-piston, but the widening of the ΔV-piston encompasses larger volumes.

Thus, the heart as a ΔV-pump adapts its size and form in relation to the incoming flow and heart rate.

The filling pressures of the right and left heart halves, respectively, determine the pressure gradient over the ventricular septum. The pressure gradient determines the shapes and positions of the ventricular septum between the right and left ventricles.

This state and state 2 and 3 form, together with the previous state (which is state 7), the prerequisite for the double regulating function of the ventricular septum.

State 2

Atrial Systolic Phase.

According to established teaching the atrial systolic contraction and its associated ECG-signal was the starting point when describing the heart's pumping function. The time between two atrial contraction was denoted a heart period or a heart cycle.

The discovery that the heart works as a ΔV-pump implies that its pumping and regulating functions mainly are controlled by the incoming flow which in turn implies that a description of a heart cycle as a logical discrete time related state diagram best is described by starting with the slow ΔV phase. For practical and ECG reasons it can be convenient to start the state diagram with the atrial contractions. The results of the atrial systolic phase depends upon many different parameters and may under certain circumstances result in that the atrial contractions do not add anything to the heart's pumping function, whereas during other circumstances it gives life-sustaining contribution.

During low rates and reduced momentum behind the ΔV-functions in state 7, the atrial contractions contribute to lift the ΔV-piston above its neutral position in state 1. The atrial contraction is a rapid activity. The hydraulic attachments of the atria and its auricles to the pericardia and to the spherical part of the ΔV piston create during atrial contractions a withdrawal sliding motion on the top of the relaxed and formable ΔV piston and along the pericardial sac. This will create a hydraulic power that forces the ΔV piston in the direction to the top of the heart. During the contraction there will be a redistribution of the blood volume between the atrias and ventricles at a minimum of external and internal acceleration of masses. The pulling of the ΔV piston to the top of the heart is favoured by quick atrial contractions because then the momentum against motions of the inner and outer masses are large. Since the total volume of the heart is fairly constant during the atrial contraction the sliding motions of the ΔV-piston against the pericardial sac only results in a redistribution of blood between the atria and the ventricles. The more or less only areas that can generate a need of external inflow volumes during atrial systole are the outflow tracts of T-pulmonalis and Aorta. These areas can generate both direct and indirect ΔV-volumes. During atrial contraction there is an inflow to the right atria but usually there is a small backflow from the left atria. This is most likely depending of small compliance volumes in the pulmonary veins and the fact that the left auricle is squeezed between the ΔV-piston and the lung veins and thus widening the veins during a withdrawal contraction. During large flows and high heart rates, with large momentum behind the rapid return of the ΔV-piston, the flow dynamics behind the ΔV-functions force the ΔV-piston to passes its neutral position. The role of the slow ΔV phase bringing the heart to a full size ΔV-pump is reduced, due to large dynamic forces and a background of static forces that can keep the heart at full size. The atrial contraction can more or less not contribute to any further motion of the ΔV-piston to the heart base.

During small ΔV-piston movements, caused by a lot of reasons, low momentum behind the returning motions of the ΔV-piston, phase 6, the atrial contraction can contribute, up to 60%, of the stroke volume by lifting the ΔV-piston to the base of the heart.

The mechanism behind the dramatic differences regarding the importance of the atrial contraction during high and low flows and rates, respectively, and during heart failure, has never had any mechanical explanations before. That is also true for the role that the auricles play for the pumping function. The heart as a ΔV-pump gives an important mechanical explanation of the atrial contraction and the auricles role for the pumping function.

It also explains why the inflow to the heart can continue despite ongoing atrial contractions.

After atrial systole follows the ventricular systolic expelling phase, here divided in three states. Since the pressure during this phase usually is much higher in the left ventricle, the left ventricle can be looked upon being a separate ΔV-pump working in collaboration with the ΔV heart pump.

State 3
Presystolic Volume to Tension Phase

After the atrial contraction the conduction system, after a certain AV-delay, in synchronised orders, starts to depolarise muscle cells in the ventricles. During state 3 (earlier called the iso-volumetric phase) the muscle not only has to create power to the heart but also has to, being the construction material, strengthen the parts of the heart that within the next time interval will be exerted by high forces.

The ventricular septum, the apical and conical parts of the ventricles and the papillary muscles will be activated first. Within a few milliseconds thereafter the initiation is spread to the rest of the heart, that means the spherical muscular sphincter like parts of the ventricles, i.e. the ΔV-piston. The way of activation of the ventricles may be regarded as a "soft start", and is useful during later phases when the ΔV-piston starts its relaxation and returning movements.

The initiation follows a pattern that optimises the presumptions of the ΔV-piston movement towards apex. Interventricular septum starts stabilizing in order to withstand the pressure gradients between the left and right ventricles. The left ventricle format with interventricular septum and its connections to the AV-ring and outflow tract of Aorta, as a direct continuation of its external shape, an internal sector of the ΔV-piston, that will interact with the volumes in the right ventricle.

The started activation of the ventricular heart muscle results in increased tensions in the heart muscles. This results in force vectors that by the construction both want to narrow the gap between the ΔV-piston and the apical-diaphragmal region of the heart and also to generate pressure gradients towards the enclosed blood volumes. The tension will create a motion in the fields where resistant against motion is lowest. The hydraulic attachments of the heart to the pericardia and the surrounding tissues creates, as is the case during the atrial contraction, sliding motions of the ventricular muscles along the pericardial sac due to that the resistance to motion of the inside and outside masses are large. An internal redistribution is obtained of the blood volume between the atria and the ventricles but in the reverse direction, resulting in closing of the valves with virtually no back-flow.

A continuing down pulling of the peripheral area of the ΔV-piston, that has a firm connection to the AV-ring and hydraulic connections to the auricles and the pericardia has a concave form in connections to the muscle mass and the enclosed blood volume. This bended form works like a first class levers and can, by bending and pulling, generate and withstand strong force gradients. Of course this needs extra strong reinforcements of circular oriented muscular fibres in the left ventricle were the pressure gradients over the ventricular wall is much higher.

It is within this bended area that the volume exchanges per stroke length unit will be greatest and it is also here and at the outflow tract of Aorta and T. Pulmonalis that the direct and indirect ΔV-volumes are generated.

In the beginning of the state the right and left ventricles are regarded as one single volume with communicating volumes to the atria and the inflow vessels. During the pull-down of the ΔV-piston and closing of the valves the pressures inside the ventricles increase. The motions of the ventricular septum now reflect what kinds of relationship there were between the static and the dynamic pressures at each side of the ventricular septum at the end of the atrial contraction, and also how the ventricular muscle is activated.

At the end of state 3 the volume redistributions have made the ΔV-piston, the AV-valves and the ventricular septum and the internal sector of the ΔV piston to start to assume the shapes and tensions they need to withstand the pressure gradients that are generated in reaching the pressures that will start an outflow from the right and left ventricles. During normal circumstances all these adaptations occur, in balance with outer resistance of fast volume changes and also concerning the motion of the ΔV-piston in balance with inner fast volume changes. Most of the inner volume changes as results of the sliding motions of the ΔV-piston are done (FIG. 4), by internal redistributions of blood volumes. The inflow to the atria can continue, especially at high flow rates, due to their relaxation especially in the areas where the auricles are covering the convex muscular parts of the ΔV-piston and in the areas around the aortic and pulmonary roots where the auricles are filling up volumes that are difficult to access.

State 3 includes many important event and time markers for the heart being a ΔV-pump and the ventricular septum being a regulator for the flow to the pulmonary and to the main circulatory system. With marking points at different locations of the ventricular septum, it can serve as a large and sensitive pressure membrane sensing the on-going activities giving lot of information about the performance of the heart and the circulatory system. This event can also be monitored by more simple registration method e.g. Apex cardiogram.

State 4
Progressive Tension and Flow Phase.

Phase 4 starts as an index mark with the opening of the aortic valve and ends as a marker on top of the aortic outflow. During this phase the motion of the ΔV-piston generates a progressive tension and flow out and into the heart. The pressure is normally much higher in the left ventricle. This results in that the ventricular septum mainly assumes the same shapes as the other parts of the left ventricle. If the systolic shapes and positions deviate from the shapes and positions before the ventricular contractions, a volume adaptation takes place between the ventricles.

As a direct continuation of state 3 the spherical ΔV-piston will create both direct and indirect ΔV-volumes. These volumes, due to external resistance and recoiling forces and increasing blood pressure inside these volumes, will give a net increase of the pressure gradients over the areas producing the ΔV-volumes.

The acceleration of a mass demands power and energy. The masses to be accelerated comprise all tissues in direct and indirect connections to the motion of the ΔV-piston. These tissues are, all blood in the heart and in the vessels entering or leaving the heart, the heart muscle itself and the masses in the heart's environment. Furthermore, energy must be added for internal and external tension and recoiling forces, and friction losses, as for example created by motions of the Aorta and T. Pulmonalis and twisting torsions of the heart.

During state 4 larger counter forces are required in order to pull the ΔV-piston towards apex. Due to that and the hydraulic attachments of the heart to the pericardial sac that in turn is hydraulically attached to the chest wall, an increased up-movement takes place of the conical part of the ventricular cylinder in parallel with the chest wall. The phenomena can be mimicked with a vacuum cup that can slide on a slippery surface with forces parallel to the surface but give a high resistance to right angel forces.

Nature has fixated the pericardial sac with strong connected tissues to the diaphragm muscle but not to sternum where the sac more or less is fixated by a hydraulic coupling. This arrangement avoids problems concerning the breathing mechanism.

The fixation of the pericardial sac, in this way renders the apical diaphragma region of the pericardial sac to act as a resilient suspension that results in a bending and lifting of Apex and the diaphragm against the chest wall. This suspension will more or less take care of all the counteracting forces that the ΔV-piston creates. Most of the counteracting resistant and recoiling forces are generated outside the common ΔV-piston by the creation of the ΔV-volumes and pulling and twisting the Aorta and T. Pulmonale. The counteracting forces between the ΔV-piston and the diaphragm area want to separate these areas in both directions. These events and energy will be regained to the pumping functions in the following phases. At high compliance and low resistance this state will be longer than at low compliance and high resistance. This may be a good diagnostic tool.

By performing measurements during this phase with even simple methods or devices like pulse plethysmography e.g. Apex cardiogram and referring these data to the heart being a ΔV heart pump will in many cases give enough information about the hearts pumping and regulating functions within a specific circulatory system.

State 5
Regressive Flow and Tension Phase

This phase is in a direct continuation of phase 4 and ends as a marker with the closing of the aortic valve. During this phase both flow and tension starts to decline in the left ventricle that can be looked upon being a separate ΔV-pump working in collaboration with the ΔV heart pump. After phase 4 the declining movement of the ΔV-piston starts. The ΔV-volumes will still be formatted though the indirect ΔV-volumes can be refilled by inflow to the atria and auricles. The twisting of the Aorta and Pulmonalis continue as long as there will be a net motion along the thoracic cage in the direction towards apex. The flow out through the Aorta continues as long as there is a common muscular contraction that can withstand the pressure gradients over the left ventricular walls that can be done by a first-levers function in the muscular part of the ΔV-piston. This part of the ΔV-piston and the diaphragm part of the left ventricle has external forces that together with the pressure inside the ventricle want to separate these areas from each other.

During the end of phase 5 the counter forces above the ΔV-piston decline. The reasons for that are partly that the acceleration of the masses has stopped and partly that the compliance volumes in the incoming veins to the atria and the indirect ΔV-volumes especially located in the auricles have started to be refilled. The ventricles, regarded as solid units, can start, because of stronger recoiling forces in the diaphragm area, to return to the neutral position this area had before phase 3. Due to the mechanical coupling this returning movement also results in a relative movement of the ΔV-piston, giving possibilities for continuous inflow into the atrial volumes despite that the real movement between the ΔV-piston and Apex declines and stops. In addition there is a declining pressure and flow in Aorta and in T. Pulmonalis which result in that their diameters decrease which in turn through their contact to the atria and auricles give room for continuous inflow into the atrial cylinder. The relative movement, but also the real movement of the ΔV-piston, is most pronounced in the region of the outflow tract of T. Pulmonalis.

The ongoing inflow above the ΔV-piston and the decreasing outflow from the heart will cross each other during this phase, which means that the heart will have its smallest total volume before the end of ventricular systole.

By performing measurements during this phase with even simple methods like pulse plethysmography units e.g. Apex cardiogram and referring these data to the heart being a ΔV heart pump will in many cases give enough information about the heart's pumping and regulating functions within a specific circulatory system.

This phase stops for practical reasons with the closing of the aorta valves but is in a middle of an ongoing process, further described under state 6.

State 6
Prediastolic Tension to Volume Phase

This phase was earlier called the isovolumetric diastolic phase.

This phase has a mechanical action that is running in a reverse way compared to state 3. That means that in order to release the pressure gradients in this described region, the left ventricle, there has to be an increase of the left ventricular volume. That can be done without disturbing any ongoing inlet flow to the heart and at higher heart rates and minute volumes also leave possibilities for ongoing outlet flow. The ongoing process in phase 5 with decreasing pressure gradients to the surroundings of the heart are, as earlier described, concentrated to the muscular parts of the ΔV-piston and the outflow tract of Aorta and T. Pulmonalis. Furthermore, these areas together with the areas in close connections to the diaphragm, which happens to be a part of the left ventricle, have contracting recoiling forces that want to separate these areas from each other through elongation and sliding motions of the ventricular walls along the thoracic cage. This surface of the heart also describes the longest distance between the ΔV-piston and Apex and has a very strong convex attachment of the ventricular muscles to the ΔV-ring and the sharp bend of T. Pulmonalis. This part of the ΔV-piston is well covered by the left and right auricles and need a strong support of muscle power. When that support goes down, the two areas, the ΔV-piston and diaphragm area start to be separated. This will both lead to a decrease in tension leading to internal redistributions of volumes and finally open the tricuspid and mitral valves. This event can also be monitored by more simple registration method e.g. Apex cardiogram.

State 7
Rapid ΔV-Phase.

The rapid diastolic returning movement of the ΔV-piston is a direct continuation of phase 6. An adapted relaxation means that stored energy in the surroundings, the twisting of the heart, can be released in a way that in optimal ways can bring the ΔV-piston back towards the top of the heart. The adapted relaxation creates a total release of the recoiling forces that wanted to separate the total ΔV-piston from the diaphragm area. This will add energy to the inflowing blood in the direction towards apex. Static and dynamic forces of the inflowing blood will exert a pressure on the areas that has created the ΔV-volumes, that means the ΔV-piston, and will create, by moving the ΔV-piston, a refilling of those areas. The movement of the ΔV-piston also creates a redistribution of blood between the auricles, atria and the ventricles and also in an early stage between the ventricles by a forth and back going motion of the intra ventricular septum. The enhanced dynamic forces in the directions to apex will be reversed by the ΔV-volumes (direct and indirect ΔV-volumes) that finally absorb the static and dynamic forces by filling and pressing the ΔV-piston towards the top of the heart. This action is referred to as the ΔV-function and will give the ΔV-piston a rapid diastolic return and dynamic forces behind the valves that together with the flow paradox will close the valves with no back flow. The return of the ΔV-piston will result in a thinning out of the left ventricular muscle, a motion that inside the heart will look like an internal peristaltic expansion wave front running from the ΔV-piston towards Apex.

This event can also be monitored by more simple registration method e.g. Apex cardiogram.

At low frequencies the ΔV-piston performs an overshoot and a recoiling movement. This is an effect of the forces of inertia that the blood has acquired and stored in an expanding wave behind the valves pushing the ΔV-piston in the direction of the direct and indirect ΔV-volumes. Once the dynamic forces have ceased the static forces will dominate and bring the ΔV-piston to a neutral expanding position, state 1.

At higher flows and frequencies the slow ΔV phase (state 1), the atrial systolic phase (state 2) and to a certain degree also a part of the early part of the presystolic volume to tension phase (state 3) in flow dynamics point of way will be overruled. The fast diastolic return of the ΔV-piston carried by an expanding wave with a lot of dynamic energy is followed more or less directly by the ventricular contraction (state 3). This is schematically illustrated in the state diagram of FIG. 6.

The strong expanding wave and the force of inertia will bring the ΔV-piston even higher up to the heart top than the atrial systole can do.

At high flow rates and frequencies ΔV-pumps due to the inertia of the in and outgoing fluid including the fluid in the pump will start to generate a more or less continuous outflow with no need of outlet valves. Still the inlet flow will create the ΔV-functions. The ΔV-pumps start to increase their stroke volumes above that can be calculated by the piston area times the stroke length.

These circumstances applied on the ΔV heart pump will during high inflow rate and high frequencies due to both static and dynamic forces in the blood flow keep the volumes of the heart above the ΔV-piston in a more or less full size at the time when the rapid ΔV phase starts. The volumes of the heart below the ΔV-piston will at the same time be low because the outflow inertia. This will create an increase of the ejection fraction that earlier never has been understood.

In accordance with the third embodiment of the present invention a Graphical User Interface (GUI) module according to SSM, preferably handled by IMS, has been developed.

The Heart State Analyzer (HSA) (FIG. 5), is by software and/or hardware adapted to analyze, and/or directly on-line transform input data of any activity at any point within the modules of SSM to discrete and/or dynamic time related state diagrams that by GUI graphically can be displayed. Input data may be collected data from various investigating methods and areas inside and outside the heart.

Signals to be used may vary in quality depending on investing tool and investigated areas. With less input data less detailed state diagrams can be presented. Since the mechanics behind the functions of the heart are known and represented by the interacting modules in SSM the need of detailed information can dramatically be reduced. Missed crucial information may be added during the next heart beat at the same or other investigated areas with the same and/or other investigating methods. This means that different investigating methods and investigated sites can be mixed to generate more detailed state diagrams even down to the micro level of the heart muscle cell and optionally the circulatory system.

SSM can graphically, by the GUI, be described with two types of state diagrams. One is classified as a discrete time related state diagram. The other is classified as a dynamic time related state diagram.

Discrete time-related state diagrams are state diagrams that present events in time related steps. Information between these steps is not displayed.

Investigating methods like echocardiography can by e.g. Tissue Velocity Imaging (TVI) produce data that by HSA and GUI according to SSM preferably handled by IMS simultaneously can transform into two discrete interacting time-related state diagrams. One represents a diagram from the right side of the heart and the other represents a diagram from the left side of the heart. This is illustrated in FIGS. 7A and 7B, where the outer ring represents the left side of the heart, and the inner ring represents the right side of the heart. The difference in timing between the defined states of the left and right state diagrams at rest and during different flow, pressure, frequencies, medications etc. will be of great value for evaluations of the hearts functions. Since the defined states are set by velocity tracking with high resolutions this will be an easy and stable documentation even at high workloads, e.g. working tests.

Implantable devices, like pacemakers, cardioverters and defibrillators, may easily, with various types of sensors, pick up physiological activities, and by an implemented HSA transform these to time related discrete or dynamic state diagrams, in order to analyze, communicate, regulate and optimize medical treatments and the variables of the device to create e.g. efficient heart activities in relations to coronary flow.

Many investigating methods have limitations in their frame rates and thus, wanted or not, most functions of the heart are by definition presented by discrete time-related state diagrams. However in many cases the sampling rates are high enough to depict dynamic events and can thus produce data that by HSA can be delivered as dynamic time related state diagrams.

Since the modules in SSM are interacting and these interactions are known, there are great opportunities to create interacting state diagrams that graphically describe the pumping and regulating functions of the heart, and optionally the circulatory system, down to molecular levels.

FIG. 7A-7B are examples where, in FIG. 7A two, and in FIG. 7B three, discrete time interacting, time related state diagrams are used to, in a very fast and easy way, display the interacting mechanical functions between the right and left ventricles. The zone between the circular state diagrams representing a whole heart cycle will be used to as a dynamic time related state diagram show the true motions of the Intra Ventricular Septum (IVS).

FIG. 8 is an example where a discrete time related state diagram is superimposed a dynamic state diagram referred to the motions of a point in the DeltaV-piston at the lateral part of the left ventricle.

Recording methods like Echocardiography, Spin CT, MRI and gamma cameras can all be used to depict motions of the total heart and structures inside the heart including flow to and from the heart and the hearts own circulatory system. They can also to some extent display pressures. They can all present motions of the heart by 2D sector scanning or frames with frame rates at "normal width" at approximately 200, 60, 30 frame rates/minute, respectively. They are all objects for making 3D visualizations with a focus on the squeezing motions of the muscles. According to this 3D acquire high computer capacities, reduces the frame rates and make low resolutions and inexact calculations. Still they do not present the mechanical functions of the heart.

They can detect and display local heart muscles disturbances like infarcted and ischemic areas, conduction faults leading to dyskinetic functions of the muscle cells. This is done with new algorithms like Tissue Velocity Imaging (TVI) that even at high frequencies can display muscular activities. The TVI signals are quite resistant to noise and are suitable input signals for HSA to present as time related state diagram according to SSM at any site both inside and outside the heart.

Strain Rate Imaging (SRI) is another new algorithm/method that can be used to measure deformation velocities in longitudinal directions (lengthening and shortening) and/or in lateral directions (thinning and thickening). The latter method is good in finding regional defects in the muscles but is too slow and makes artifacts at high heart rates According to SSM the muscle volumes can more or less by IMM (FIG. 5) be separated from heart as a cluster state machine to create the DeltaV-Heart state machine (FIG. 3). This will focus the investigating method on the contours that by motions creates the pumping and regulating functions of the heart (FIG. 4A-4D). These active contours and close related areas have during the whole heart cycle fairly smooth and known shapes and interactions that, by HSA and HSV in 1D-3D e.g. by mapping (described above), can be detected and used to calculate and validate events, volume and volume changes inside and outside the heart during the whole heart cycle. Volumes like DeltaV volumes, resilient suspension volumes, in and outflow volumes, volume to tension and tension to volumes, regulating volumes, regurgitation volumes, and other volume changes due to mal functions of the heart can be quantified and displayed.

Mapping measurements creating a 1D-3D representation of the heart according to SSM managed by IMM and preferably IMS (FIG. 5) is very suitable not only to present the mechanical activities of the pumping and regulating functions, but can also be developed into a method describing the interactions between the pumping and regulating functions of the heart. This can e.g. be done by dynamic triangular measurements adapting one or more points at IVS and the other points at the Right respectively the Left Delta-V pump piston and possibly at other contours and areas of RV and LV. This triangulating method may further in the same way be used to measure the rearrangement motions of the muscle volumes used to e.g. be compared with motions of the pumping and regulating areas. The mapping and triangular method creating 1D-3D representing the interacting functions of the heart does not need the same computer power, can increase the frame rates, can produce validated data and quantify various types of volumes and volume shifts. It can also be used to create simple and fast investigating methods.

All structures inside the pericardial sac including the heart's own internal circulatory system are theoretically incompressible. The muscle cells way of working by shortening and thickening would with unorganized contractions and relaxation due to the constant volume, in a perfect mismatch and resistance (e.g. ventricular fibrillations), lead to muscular volume rearrangement but not lead to any useful mechanical work and thus reduce the efficient rate of power to useful pumping and regulating functions down to zero.

In accordance with the fourth embodiment of the present invention an Efficient Rate Analyzer (ERA) module is created by comparing the outcome of the mechanical functions of the heart with the heart muscular rearrangements according to SSM preferably managed by IMS. This can be used to calculate and optionally enhance the efficient rate of the muscles as construction material and power source.

This can, according to FIG. 9, be done by implementing IMM and modules like HSA, HSV, ERA and GUI according to SSM and optionally handled by IMS in existing investigating methods like Echocardiography, Spin CT, MRI and gamma cameras. By combining state diagrams of mechanical functions with state diagrams of muscular rearrangement, e.g. by triangulating, tissues velocity curves, (FIG. 7B) there will be possibilities to calculate and by e.g. pacemakers improve the efficient rates.

Since the interactions of the mechanics behind the functions of the heart according to SSM are known there are in most of the cases no needs to have full 3D examinations. By using the dynamic triangulating method in one or more sectors of the heart especially with added muscular rearrangement patterns as in FIG. 7B, will in many cases create sufficient diagnostic proof of the mechanical pumping and regulating functions of the heart.

These arrangements can also be used to create less advanced and less expensive and faster investigating methods as described above.

According to the fifth preferred embodiment of the present invention a Heart State Analyzer (HSA) is created, and optionally the circulatory system including the coronary system (FIG. 2) according to SSM preferably managed by IMS. This simulator can be used for learning purposes and simulate what impacts different kinds of boundary conditions changes will have on the modules of SSM. This means that medical and surgical treatment as well as other factors that can have impacts on the heart and circulatory systems can be simulated.

According to the sixth preferred embodiment of the present invention an information system is created that with reference values manually and or automatically can support and improve the analyzing and simulation modules according to SSM preferably handled by IMS. They can be very useful in supporting what kinds of impacts different medical and surgical treatments will have on the heart and circulatory systems according to the modules of SSM. The database systems can also serve as reference standards for e.g. treatments, as well as follow-up for e.g. patients (individual dose response treatments), health-care and training athletes.

According to the seventh preferred embodiment of the present invention simple investigating units are created, like pressure sensors, microphones, photo sensors, oxymeters etc, that equipped with HSA and GUI according to SSM, preferably handled by IMS, can create discrete and/or dynamic time related state diagrams, to be used both inside and outside the body that manually and/or automatically, e.g. by telemedicine, can serve as control devices for the heart and optionally the circulatory system of an individual.

FIG. 10 is an example of a blood pressure unit equipped with IMM and the modules HSA and GUI according to SSM handled by IMS State diagrams monitored from the surroundings of the heart will more or less be referred to as functions of the left ventricle. One exception might be the motion of the Apical-Diaphragm part that most probably to some extent reflects the inflow to the right ventricle. This sensor, preferably implemented as velocity sensors attached on the surface of a body close to apex, larger arteries and capillaries, can, beat by beat, in real time, collect enough data to generate state diagrams that may be used as control functions of an individual's heart and circulatory system.

Mechanical activities produced by the heart result in hydraulic work both into and out of the heart. The compliance and resistance of the vessels and to a certain extent their own activities will create distortions of the original activities. By comparing time related state diagrams generated close to the heart, e.g. by Apex cardiogram and/or ultra sound, with time-related state diagrams over larger arteries, e.g. by pressure sensors or microphones and even at capillary levels (e.g. oxymeters), these distortions compared at rest and also during work can be "normalized". This will generate individually related transforming values that can be of diagnostic value concerning the circulatory system, and also render to new individual specific time related state diagrams presented by GUI that can bring information about the mechanical activities of the heart according to SSM.

A typical graphical display of such a device could very much look like that in FIG. 7A-7B including other related information's observed by ECG, blood pressure monitoring, breathing, chest pains, lactose's feelings and warning signals etc. These time-related state diagrams are very easy to analyze and communicate. Ordinary people, interested in following up medication and or training effects can use devices like this to create time related state diagrams that manually and/or automatically can by e.g. via cell phones be linked to databases and/or to medical care centers for e.g. evaluations. Since it is known that the coronary flow is reduced close to zero during ventricular systole, time-related state diagram also can be used as an optimizing, diagnostic and warning system.

The state space model and all related modules according to the present invention are realized by computer software and hardware means, either by using standard computer software or by specifically designed software. The information may be organized in databases, preferably in relational databases. The processing means may be a personal computer, a microprocessor or a specific dedicated device.

The present invention is not limited to the above-described preferred embodiments. Various alternatives, modifications and equivalents may be used. Therefore, the above embodiments should not be taken as limiting the scope of the invention, which is defined by the appending claims.

The invention claimed is:

1. A state space model (SSM), being a computer-calculated model, adapted to represent pumping and controlling functions of a heart that have been determined by a heart cluster state machine simulating the heart of an individual and optionally the circulatory system of an individual,
wherein,
the state space model is adapted to transform all muscular cell functions, except their volumes, to incomplete and/or complete wire frames and/or surface mesh models of the heart and optionally the circulatory system with impacts of boundary conditions concerning the model, and
the state space model comprises two groups of separate interacting state machines, (1) heart muscle cell state machines and (2) DeltaV-pump state machines,
the heart muscle cell state machines comprising a main module describing construction and boundary conditions of a working cardiac muscle cell and their interrelations on a molecular level, with an internal module, leaving muscle cell volumes outside, describing cardiac muscle cell functions including a conducting system as construction material and power source with possibilities to be reluctant by elongation, firm by static work and create dynamic work by shortening, to be transferred to the contours and areas determined by the DeltaV-pump state machines.

2. The state space model according to claim 1, wherein the DeltaV-pump state machines comprise a main module divided into sub-modules schematically showing a construction of the heart as a geometric description of the heart in two and/or three dimensions as a mechanical device made by a fusion of two Delta-pump state machines, creating the right and left side of the heart.

3. The state space model according to claim 2, wherein the DeltaV-pump state machines further comprise:
an Intra Ventricular Septum module (IVS) describing constructions and functions of Intra Ventricular Septum as a result of the fusion of the two DeltaV-pump state machines generating a third DeltaV-pump state machine;
a Delta-V piston (DVP) module describing a construction and function of the Delta-V piston;
a RA-LA construction module describing construction and functions of the right and left atria and auricle constructions; and
a displacement pump state machine module consisting of lines, wire frames and/or surface mesh of outer contours and optionally inner contours of the muscle volumes in one, two or three dimensions.

4. The state space model according to claim 1, wherein the SSM is analyzed by a Heart State Analyzer (HSA) that presents the data as discrete and/or dynamic state diagrams, optionally handled and organized by an Interconnecting Management System (IMS).

5. The state space model according to claim 4, wherein a Graphical User Interface (GUI) module graphically presents one or several interacting discrete and/or dynamic time correlated state diagrams, optionally handled and organized by an Interconnecting Management System (IMS), obtained by the HSA describing the pumping and regulating functions of the heart and optionally the circulatory system.

6. The state space model according to claim 1, wherein an Efficiency Rate Analyzer (ERA) module is connected to the SSM, optionally handled and organized by an Interconnecting Management System (IMS), to compare an outcome of the mechanical functions of the heart with the heart muscular rearrangements obtained by the SSM, the ERA configured to present and optionally enhance an efficient rate of the muscles as construction material and power source.

7. The state space model according to claim 1, wherein a Heart State Simulator (HSS) is connected to the SSM for learning purposes and to simulate impacts that different kinds of boundary conditions changes will have on the modules of the SSM, optionally handled and organized by an Interconnecting Management System (IMS).

8. The state space model according to claim 5, wherein the SSM is arranged in an investigating device, a pressure sensor, a microphone, a photo sensor or a oxymeter, and includes HSA and GUI, to create discrete and/or dynamic time related state diagrams.

9. The state space model according to claim 4, wherein the model creates investigating methods in one, two and/or three dimensions by mapping interacting points, contours and/or areas correlated to the pumping and regulating functions of the heart by dynamic triangular measurements calculated by HSA according to the SSM, optionally handled and organized by an Interconnecting Management System (IMS).

10. The state space model according to claim 5, wherein the Graphical User Interface (GUI) module graphically presents one or several interacting discrete and/or dynamic time correlated state diagrams, optionally handled and organized by an Interconnecting Management System (IMS), obtained by (HSA) describing the pumping and regulating functions of the heart and optionally the circulatory system.

* * * * *